(12) United States Patent
Farrand

(10) Patent No.: US 7,771,801 B2
(45) Date of Patent: Aug. 10, 2010

(54) CHIRAL COMPOUNDS

(75) Inventor: Louise Diane Farrand, Blandford Forum (GB)

(73) Assignee: Merck Patent GmbH, Darmstadt (DE)

( * ) Notice: Subject to any disclaimer, the term of this patent is extended or adjusted under 35 U.S.C. 154(b) by 3 days.

(21) Appl. No.: 12/088,535

(22) PCT Filed: Sep. 20, 2006

(86) PCT No.: PCT/EP2006/009134

§ 371 (c)(1),
(2), (4) Date: Mar. 28, 2008

(87) PCT Pub. No.: WO2007/039105

PCT Pub. Date: Apr. 12, 2007

(65) Prior Publication Data

US 2008/0281108 A1    Nov. 13, 2008

(30) Foreign Application Priority Data

Sep. 30, 2005   (EP) ................................. 05021491

(51) Int. Cl.
*C09K 19/58*   (2006.01)
*C09K 19/38*   (2006.01)
*C09K 19/34*   (2006.01)
*C09K 19/32*   (2006.01)
*C07D 321/10*  (2006.01)

(52) U.S. Cl. ..................... 428/1.1; 428/1.3; 252/299.01; 252/299.2; 252/299.61; 252/299.62; 549/348

(58) Field of Classification Search ................ 549/348; 252/299.01, 299.61, 299.62, 299.5, 299.2; 428/1.1, 1.3

See application file for complete search history.

(56) References Cited

U.S. PATENT DOCUMENTS

| 6,818,261 B2 | 11/2004 | Kawabata |
| 6,835,427 B2 | 12/2004 | Motoyama et al. |
| 6,916,940 B2 | 7/2005 | Kirsch et al. |
| 7,642,035 B2 * | 1/2010 | Shukla et al. .......... 430/270.11 |
| 2004/0054196 A1 | 3/2004 | Kirsch et al. |

FOREIGN PATENT DOCUMENTS

| EP | 1 326 854 B1 | 6/2004 |
| JP | 2002 179668 A2 | 6/2002 |
| JP | 2002 179669 A2 | 6/2002 |
| JP | 2005 113131 A2 | 4/2005 |
| WO | WO 02 34739 A1 | 5/2002 |

OTHER PUBLICATIONS

Wong M S et al: "Synthesis of Novel Non-Centrosymmetric Crystalline Materials for Quadratic Non-Linear Optics" Journal of the Chemical Society, Chemical Communications, Chemical Society. Letchworth, GB. No. 3, 1994, pp. 249-250, XP00205516.
Wong M S et al: "Novel Approach in Molecular Design for Quadratic Nonlinear Optics (NLO): Design, Synthesis and Characterizations of New Classes of Dipolar and Multi-Dipolar Molecules" Molecular Crystals and Liquid Crystals Science and Technology. Section B. Nonlinear Optics, Gordon and Breach Science Publishers, US. vol. 9, No. ¼, 1995, pp. 181-186 XP002103114.
Man Shing Wong et al: Intramolecular Dipolar Coupling Enhancement of the First-Order Molecular Hyperpolarizability in a Polar Solvent Chemical Physics Letters, North-Holland, Amsterdam, NL. vol. 253, No. ½ (Apr. 26, 1996) XP009057255.
Schafer et al: "Efficient Diastereoselective Synthesis of Chiral Macrocycles via Zirconocene Coupling. Synthetic Control of Size and Geometry" journal of the American chemical society, vol. 123, 2002, p. 2683-2684, XP002413264.
P. Magliolo et al, "Binaphtol systems", "Highly diastereoselective reduction and addition of nucleophiles to binaphthol-protected arylglyoxals", Tet Asymm, 1992, pp. 365-366, vol. 3, No. 3.

* cited by examiner

*Primary Examiner*—Shean C Wu
(74) *Attorney, Agent, or Firm*—Millen, White, Zelano, Branigan, P.C.

(57) ABSTRACT

The invention relates to chiral compounds, methods of their preparation, and to their use in optical, electrooptical, electronic, semiconducting or luminescent components or devices, and in decorative, security, cosmetic or diagnostic applications.

19 Claims, No Drawings

CHIRAL COMPOUNDS

FIELD OF THE INVENTION

The invention relates to chiral compounds, methods of their preparation, and to their use in optical, electrooptical, electronic, semiconducting or luminescent components or devices, and in decorative, security, cosmetic or diagnostic applications.

BACKGROUND AND PRIOR ART

Chiral liquid crystal (LC) materials are useful for many applications, for example LC displays (LCD) or polymer films with a twisted structure. Usually they consist of an LC host material containing one or more chiral dopants which induce the desired helical twist. The effectiveness of a chiral compound to induce a helically twisted molecular structure in a liquid crystal host material is described by its so-called helical twisting power (HTP). The HTP is given in first approximation, which is sufficient for most practical applications, by equation (1):

$$HTP = \frac{1}{p \cdot c} \quad (1)$$

wherein c is the concentration of the chiral compound in the host material and p is the helical pitch.

As can be seen from equation (1), a short pitch can be achieved by using a high amount of the chiral compound or by using a chiral compound with a high absolute value of the HTP. Thus, in case chiral compounds with low HTP are used, high amounts are needed to induce a short pitch. This is disadvantageous, because the chiral compounds known from prior art do often negatively affect the properties of the LC host mixture like the clearing point, dielectric anisotropy, viscosity, driving voltage or switching times, and because chiral compounds can be used only as pure enantiomers and are therefore expensive and difficult to synthesize.

Another disadvantage of prior art chiral compounds is that they often show low solubility in the LC host material, which leads to undesired crystallization at low temperatures. To overcome this disadvantage, typically two or more different chiral dopants have to be added to the host mixture. This implies higher costs and does usually also require additional effort for temperature compensation of the material, as the different dopants have to be selected such that their temperature coefficients of the twist compensate each other.

Consequently, there is a considerable demand for chiral compounds with a high HTP which are easy to synthesize, can be used in low amounts, show low temperature dependence of the twisting power e.g. for utilizing a constant reflection wavelength, show good solubility in an LC host material and do not have a negative influence on the properties of the LC host.

The invention has the aim of providing chiral compounds having these properties, and not having the above-mentioned disadvantages of prior art chiral compounds. Another aim of the invention is to extend the pool of chiral compounds available to the expert. Other aims are immediately evident to the expert from the following description.

The inventors of the present invention have found that these aims can be achieved by providing chiral compounds as claimed in this invention, which comprise a 6,6'-bisalkinyl-1,1'-bi(2-naphthol) group.

Chiral binaphthol derivatives with alkinyl groups are disclosed in JP 2002-179668 A, JP 2002-179669 A, J. Am. Chem. Soc. 2001, 123(11), 2683, Chem. Phys. Letters 1996, 253(1,2), 141, Mol. Cryst. Liq. Cryst. S&T, Section B 1995, 9, 181, and J. Chem. Soc., Chem. Commun. 1994, 3, 249. However, compounds as claimed in the present invention are not disclosed.

SUMMARY OF THE INVENTION

The invention relates to compounds of formula I

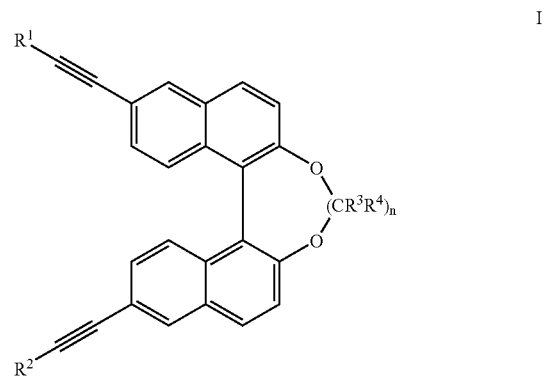

wherein
$R^1$ and $R^2$ independently of each other denote H, F, Cl, Br, I, CN, NCS, $SF_5$, or straight-chain, branched or cyclic alkyl, aryl or heteroaryl having 1 to 30 C-atoms that is optionally mono- or polysubstituted by F, Cl, Br, I or CN, and in which one or more non-adjacent $CH_2$ groups are optionally replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CY$^1$=CY$^2$— or —C≡C— in such a manner that O and/or S atoms are not linked directly to one another, or denote -(Z$^1$-A$^1$)$_m$-R$^5$ or P-Sp-,
$R^3$ and $R^4$ independently of each other have one of the meanings of $R^1$,
$R^5$ is H, F, Cl, Br, I, CN, NCS, $SF_5$, or straight-chain or branched alkyl having 1 to 30 C-atoms that is optionally mono- or polysubstituted by F, Cl, Br, I or CN, and in which one or more non-adjacent $CH_2$ groups are optionally replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CY$^1$=CY$^2$— or —C≡C— in such a manner that O and/or S atoms are not linked directly to one another, or denotes P-Sp-,
P is a polymerizable group,
Sp is a spacer group or a single bond,
$A^1$ is, in case of multiple occurrence independently of one another, an aromatic or alicyclic group, which optionally contains one or more hetero atoms selected from N, O and S, and is optionally mono- or polysubstituted by $R^1$,
$Z^1$ in case of multiple occurrence independently of one another denotes —O—, —S—, —CO—, —COO—, —OCO—, —S—CO—, —CO—S—, —O—COO—, —CO—NR$^0$—, —NR$^0$—CO—, —NR$^0$—CO—NR$^{00}$, —NR$^0$—CO—O—, —O—CO—NR$^0$—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —(CH$_2$)$_4$—, —CF$_2$CH$_2$—, —CH$_2$CF$_2$—, —CF$_2$CF$_2$—, —CH=N—, —N=CH—, —N=N—, —CH=CR⁰—, —CY¹=CY²—, —C≡C—, —CH=CH—COO—, —OCO—CH=CH— or a single bond, R⁰ and R⁰⁰ independently of each other denote H or alkyl with 1 to 12 C-atoms, Y¹ and Y² independently of each other denote H, F, Cl or CN, m is 0, 1, 2, 3 or 4, n is an integer from 2 to 5, with the proviso that, if n is 3 and all R³ and R⁴ are H, then R¹ and R² are not 4-cyanophenyl.

The invention further relates to an LC material comprising one or more compounds of formula I.

The invention further relates to a chiral anisotropic polymer obtained by polymerizing a compound of formula I or an LC material as described above and below, preferably in its oriented state in form of a thin film.

The invention further relates to the use of compounds, materials and polymers as described above and below in electrooptical displays, LCDs, optical films, polarizers, compensators, beam splitters, reflective films, alignment layers, colour filters, holographic elements, hot stamping foils, coloured images, decorative or security markings, LC pigments, adhesives, cosmetics, diagnostics, nonlinear optics, optical information storage, electronic devices, organic semiconductors, field effect transistors (FET), components of integrated circuitry (IC), thin film transistors (TFT), Radio Frequency Identification (RFID) tags, organic light emitting diodes (OLED), electroluminescent displays, lighting devices, photovoltaic devices, sensor devices, electrode materials, photoconductors, electrophotographic recording, lasing materials or devices, or as chiral dopants.

TERMS AND DEFINITIONS

The term "film" includes rigid or flexible, self-supporting or freestanding films with mechanical stability, as well as coatings or layers on a supporting substrate or between two substrates.

The term "liquid crystal or mesogenic material" or "liquid crystal or mesogenic compound" means materials or compounds comprising one or more rod- or board-shaped (calamitic) or disk-shaped (discotic) mesogenic groups, i.e. groups with the ability to induce liquid crystal (LC) phase behaviour. The compounds or materials comprising mesogenic groups do not necessarily have to exhibit an LC phase themselves. It is also possible that they show LC phase behaviour only in mixtures with other compounds, or when the mesogenic compounds or materials, or the mixtures thereof, are polymerized.

For the sake of simplicity, the term "liquid crystal material" is used hereinafter for both mesogenic and LC materials.

Polymerizable compounds with one polymerizable group are also referred to as "monoreactive" compounds, compounds with two polymerizable groups as "direactive" compounds, and compounds with more than two polymerizable groups as "multireactive" compounds. Compounds without a polymerizable group are also referred to as "non-reactive" compounds.

The term "reactive mesogen" (RM) means a polymerizable mesogenic or liquid crystal compound.

The binaphthyl group shown in the formulae above and below includes both the S,S- and R,R-isomer.

DETAILED DESCRIPTION OF THE INVENTION

The compounds of formula I have several advantages they can easily be synthesized, also on large scale of several hundred grams, with a broad range of derivatives using standard methods that are known from the literature, the starting materials, S,S-binaphthol or R,R-binaphthol, can be obtained commercially, they can be prepared enantiomerically pure as compounds of different handedness (left handed and right handed), enabling both left and right handed helices to be formed in a nematic host, they exhibit a high HTP, they exhibit a good solubility in LC mixtures, they are mesogenic or even liquid crystalline, when used as chiral dopants in an LC host material they do not negatively influence the LC phase of the host.

Especially preferred are compounds of formula I, wherein

R¹ and R² are identical groups,

R¹ and/or R² are P-Sp-, wherein Sp is preferably —(CH₂)_z— with z being an integer from 1 to 12, preferably 1 to 6, most preferably 1, R¹ and R² are optionally fluorinated alkyl with 1 to 12 C atoms, the compounds comprise at least one group P-Sp-, n is 2, 3, 4 or 5 and all of R³ and R⁴ denote H, n is 2, 3, 4 or 5 and one or more of R³ and R⁴ denote alkyl or alkoxy with 1 to 12 C atoms, n is 2, 3, 4 or 5 and one or more groups CR³R⁴ denote CH-(Z¹-A¹)_m-R⁵, with R⁵, Z¹, A¹ and m being as defined above, R⁵ is P-Sp-, R⁵ is alkyl or alkoxy with 1 to 12 C atoms that is optionally fluorinated, n is 2, 3, 4, 5 or 6, m is 1, 2 or 3.

Preferred cycloalkyl, aryl and heteroaryl groups include, without limitation, furan, pyrrol, thiophene, oxazole, thiazole, thiadiazole, imidazole, phenylene, cyclohexylene, bicyclooctylene, cyclohexenylene, pyridine, pyrimidine, pyrazine, azulene, indane, naphthalene, tetrahydronaphthalene, anthracene and phenanthrene, all of which are optionally substituted by one or more groups L, with L having one of the meanings of R¹ given in formula I.

Particular preferred cycloalkyl, aryl and heteroaryl groups are selected from 1,4-phenylene, pyridine-2,5-diyl, pyrimidine-2,5-diyl, thiophene-2,5-diyl, naphthalene-2,6-diyl, 1,2,3,4-tetrahydronaphthalene-2,6-diyl, indane-2,5-diyl, bicyclooctylene or 1,4-cyclohexylene wherein one or two non-adjacent CH₂ groups are optionally replaced by O and/or S, wherein these groups are unsubstituted, mono- or polysubstituted by L as defined above.

Preferably L is selected from F, Cl, Br, I, —CN, —NO₂, —NCO, —NCS, —OCN, —SCN, —C(=O)NR⁰R⁰⁰, —C(=O)X, —C(=O)R⁰, —NR⁰R⁰⁰, —OH, —SF₅, wherein R⁰, R⁰⁰ and X are as defined above, optionally substituted silyl, aryl with 1 to 12, preferably 1 to 6 C atoms, and straight chain or branched alkyl, alkoxy, alkylcarbonyl, alkoxycarbonyl, alkylcarbonlyoxy or alkoxycarbonyloxy with 1 to 12, preferably 1 to 6 C atoms, wherein one or more H atoms are optionally replaced by F or Cl.

More preferably L is selected from F, Cl, CN, NO₂ or straight chain or branched alkyl, alkoxy, alkylcarbonyl, alkoxycarbonyl, alkylcarbonlyoxy or alkoxycarbonyloxy with 1 to 12 C atoms, wherein the alkyl groups are optionally perfluorinated.

Most preferably L is selected from F, Cl, CN, $NO_2$, $CH_3$, $C_2H_5$, $C(CH_3)_3$, $CH(CH_3)_2$, $CH_2CH(CH_3)C_2H_5$, $OCH_3$, $OC_2H_5$, $COCH_3$, $COC_2H_5$, $COOCH_3$, $COOC_2H_5$, $CF_3$, $OCF_3$, $OCHF_2$ or $OC_2F_5$, in particular F, Cl, CN, $CH_3$, $C_2H_5$, $C(CH_3)_3$, $CH(CH_3)_2$, $OCH_3$, $COCH_3$ or $OCF_3$, most preferably F, Cl, $CH_3$, $C(CH_3)_3$, $OCH_3$ or $COCH_3$.

Some preferred groups $-(Z^1-A^1)_m-$ are listed below. For reasons of simplicity, Phe in these groups is 1,4-phenylene, PheL is 1,4-phenylene that is substituted with 1 to 4 groups L as defined in formula I, Cyc is 1,4-cyclohexylene and Z has one of the meanings of $Z^1$ in formula I. The list is comprising the following subformulae as well as their mirror images

| | |
|---|---|
| -PheL- | II-1 |
| -PheL-Z-Phe- | II-2 |
| -PheL-Z-PheL- | II-3 |
| -Phe-Z-Cyc- | II-4 |
| -PheL-Z-Cyc- | II-5 |

Z is preferably —O—, —COO—, —OCO—, —CH=CH—, —C≡C—, —CH=CH—COO—, —OCO—CH=CH—, —$CH_2CH_2$— or a single bond.

Very preferably the group $-(Z^1-A^1)_m-$ is selected from the following formulae and their mirror images

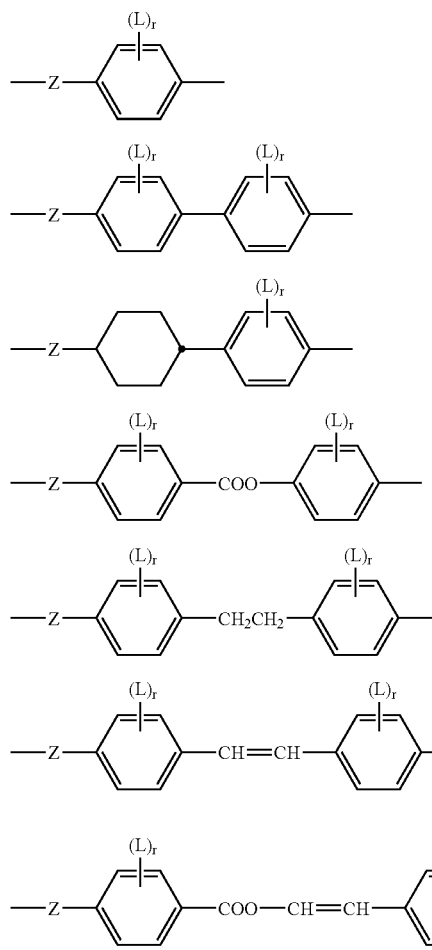

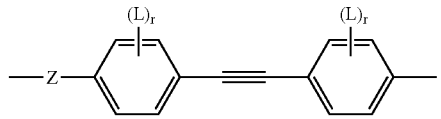

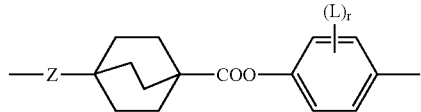

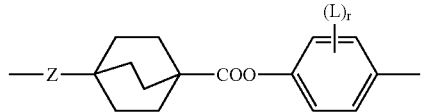

wherein L and Z are as defined above and r is 0, 1, 2, 3 or 4, preferably 0, 1 or 2.

A group

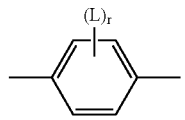

wherein r is different from 0 is preferably denotin

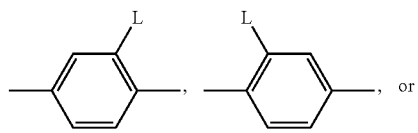

furthermore

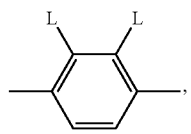

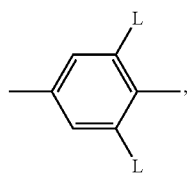

with L having each independently one of the meanings given above. Very preferred compounds of formula I comprise at least two groups

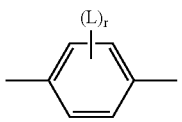

wherein r is 1 or at least one group

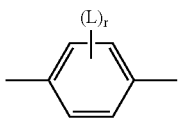

wherein r is 2.

An alkyl or alkoxy radical, i.e. where the terminal $CH_2$ group is replaced by —O—, can be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

An alkyl group wherein one or more $CH_2$ groups are replaced by —CH=CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-6-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

In an alkyl group wherein one $CH_2$ group is replaced by —O— and one by —CO—, these radicals are preferably neighboured. Accordingly these radicals together form a carbonyloxy group —CO—O— or an oxycarbonyl group —O—CO—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl, 4-(methoxycarbonyl)-butyl.

An alkyl group wherein two or more $CH_2$ groups are replaced by —O— and/or —COO— can be straight-chain or branched. It is preferably straight-chain and has 3 to 12 C atoms. Accordingly it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis(methoxycarbonyl)-ethyl, 3,3-bis-(methoxycarbonyl)-propyl, 4,4-bis(methoxycarbonyl)-butyl, 5,5-bis-(methoxycarbonyl)-pentyl, 6,6-bis(methoxycarbonyl)-hexyl, 7,7-bis-(methoxycarbonyl)-heptyl, 8,8-bis(methoxycarbonyl)-octyl, bis-(ethoxycarbonyl)-methyl, 2,2-bis(ethoxycarbonyl)-ethyl, 3,3-bis-(ethoxycarbonyl)-propyl, 4,4-bis(ethoxycarbonyl)-butyl, 5,5-bis-(ethoxycarbonyl)-hexyl.

An alkyl or alkenyl group that is monosubstituted by CN or $CF_3$ is preferably straight-chain. The substitution by CN or $CF_3$ can be in any desired position.

An alkyl or alkenyl group that is at least monosubstituted by halogen is preferably straight-chain. Halogen is preferably F or Cl, in case of multiple substitution preferably F. The resulting groups include also perfluorinated groups. In case of monosubstitution the F or Cl substituent can be in any desired position, but is preferably in ω-position. Examples for especially preferred straight-chain groups with a terminal F substituent are fluormethyl, 2-fluorethyl, 3-fluorpropyl, 4-fluorbutyl, 5-fluorpentyl, 6-fluorhexyl and 7-fluorheptyl. Other positions of F are, however, not excluded.

Halogen is preferably F or Cl.

The polymerizable group P is a group that is capable of participating in a polymerization reaction, like radicalic or ionic chain polymerization, polyaddition or polycondensation, or capable of being grafted, for example by condensation or addition, to a polymer backbone in a polymeranaloguous reaction. Especially preferred are polymerizable groups for chain polymerization reactions, like radicalic, cationic or anionic polymerization. Very preferred are polymerizable groups comprising a C—C double or triple bond, and polymerizable groups capable of polymerization by a ring-opening reaction, like oxetanes or epoxides.

Very preferably the polymerizable group P is selected from $CH_2$=$CW^1$—COO—, $CH_2$=$CW^1$—CO—,

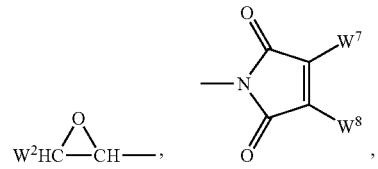

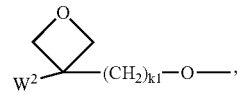

$CH_2$=$CW^2$—(O)$_{k1}$—, $CH_3$—CH=CH—O—, ($CH_2$=CH)$_2$ CH—OCO—, ($CH_2$=CH—$CH_2$)$_2$CH—OCO—, ($CH_2$=CH)$_2$CH—O—, ($CH_2$=CH—$CH_2$)$_2$N—, ($CH_2$=CH—$CH_2$)$_2$N—CO—, HO—$CW^2W^3$—,

HS—CW²W³—, HW²N—, HO—CW²W³—NH—, CH₂=CW¹—CO—NH—, CH₂=CH—(COO)$_{k1}$-Phe-(O)$_{k2}$—, CH₂=CH—(CO)$_{k1}$-Phe-(O)$_{k2}$—, Phe-CH=CH—, HOOC—, OCN—, and W⁴W⁵W⁶Si—, with W¹ being H, F, Cl, CN, CF₃, phenyl or alkyl with 1 to 5 C-atoms, in particular H, C₁ or CH₃, W² and W³ being independently of each other H or alkyl with 1 to 5 C-atoms, in particular H, methyl, ethyl or n-propyl, W⁴, W⁵ and W⁶ being independently of each other Cl, oxaalkyl or oxacarbonylalkyl with 1 to 5 C-atoms, W⁷ and W⁸ being independently of each other H, Cl or alkyl with 1 to 5 C-atoms, Phe being 1,4-phenylene that is optionally substituted by one or more groups L as defined above, and $k_1$ and $k_2$ being independently of each other 0 or 1.

Especially preferred groups P are CH₂=CH—COO—, CH₂=C(CH₃)—COO—, CH₂=CH—, CH₂=CH—O—, (CH₂=CH)₂CH—OCO—, (CH₂=CH)₂CH—O—,

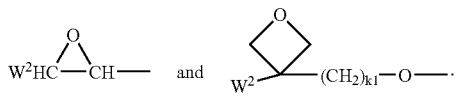

Especially preferably Pg is a vinyl group, an acrylate group, a methacrylate group, an oxetane group or an epoxy group, especially preferably an acrylate or methacrylate group.

Very preferred are acrylate and oxetane groups. Oxetanes produce less shrinkage upon polymerization (cross-linking), which results in less stress development within films, leading to higher retention of ordering and fewer defects. Oxetane cross-linking also requires a cationic initiator, which unlike a free radical initiator is inert to oxygen.

As spacer group all groups can be used that are known for this purpose to the skilled in the art. The spacer group Sp is preferably of formula Sp'-X', such that -Sp-C≡C— is -Sp'-X—C≡C—, -Sp-A$^{1/2}$- is -Sp-X-A$^{1/2}$- and P-Sp is P-Sp'-X'-, wherein Sp' is alkylene with 1 to 20 C atoms, preferably 1 to 12 C-atoms, which is optionally mono- or polysubstituted by F, Cl, Br, I or CN, and wherein one or more non-adjacent CH₂ groups are optionally replaced, in each case independently from one another, by —O—, —S—, —NH—, —NR⁰—, —SiR⁰R⁰⁰—, —CO—, —COO—, —OCO—, —OCO—O—, —S—CO—, —CO—S—, —NR⁰—CO—O—, —O—CO—NR⁰—, —NR⁰—CO—NR⁰—, —CH=CH— or —C≡C— in such a manner that O and/or S atoms are not linked directly to one another, X' is —O—, —S—, —CO—, —COO—, —OCO—, —O—COO—, —CO—NR⁰—, —NR⁰—CO—, —NR⁰—CO—NR⁰—, —OCH₂—, —CH₂O—, —SCH₂—, —CH₂S—, —CF₂O—, —OCF₂—, —CF₂S—, —SCF₂—, —CF₂CH₂—, —CH₂CF₂—, —CF₂CF₂—, —CH=N—, —N=CH—, —N=N—, —CH=CR⁰—, —CY¹=CY²—, —C≡C—, —CH=CH—COO—, —OCO—CH=CH— or a single bond, R⁰ and R⁰⁰ are independently of each other H or alkyl with 1 to 12 C-atoms, and Y¹ and Y² are independently of each other H, F, Cl or CN.

X' is preferably —O—, —S—CO—, —COO—, —OCO—, —O—COO—, —CO—NR⁰—, —NR⁰—CO—, —NR⁰—CO—NR⁰— or a single bond.

Typical groups Sp' are, for example, —(CH₂)$_p$—, —(CH₂CH₂O)$_q$—CH₂CH₂—, —CH₂CH₂—S—CH₂CH₂— or —CH₂CH₂—NH—CH₂CH₂— or —(SiR⁰R⁰⁰O—O)$_p$—, with p being an integer from 2 to 12, q being an integer from 1 to 3 and R⁰ and R⁰⁰ having the meanings given above.

Preferred groups Sp' are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

Further preferred are compounds with one or two groups P-Sp- wherein Sp is a single bond. In case of compounds with two groups P-Sp, each of the two polymerizable groups P and the two spacer groups Sp can be identical or different.

Particularly preferred compounds of formula I are those of the following formulae

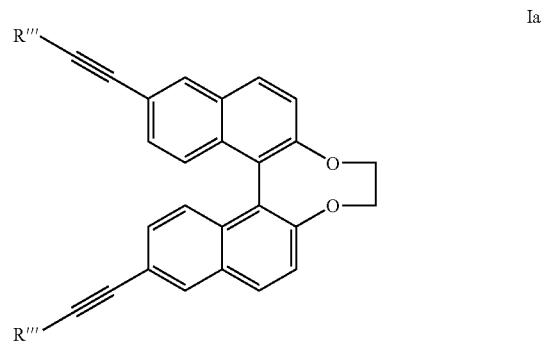

Ia

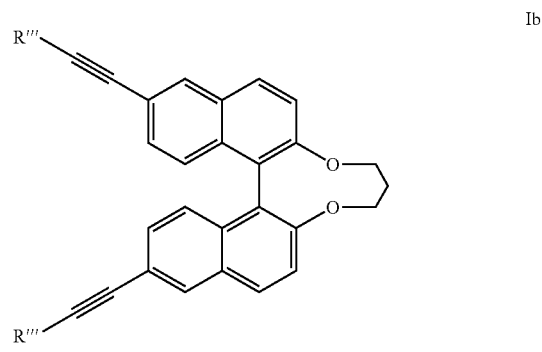

Ib

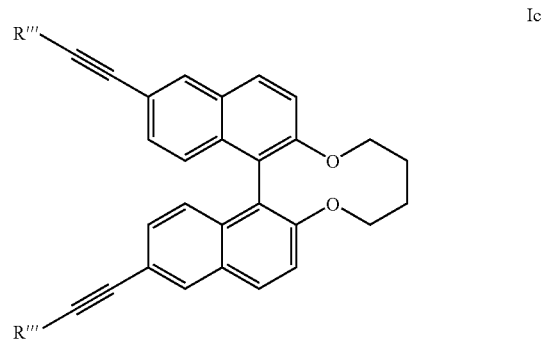

Ic

-continued

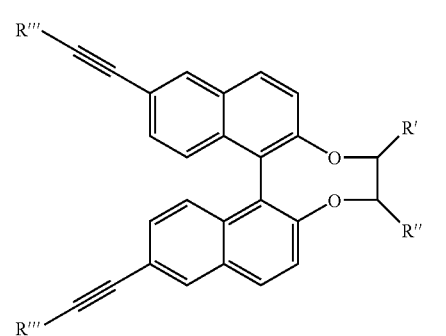
Id

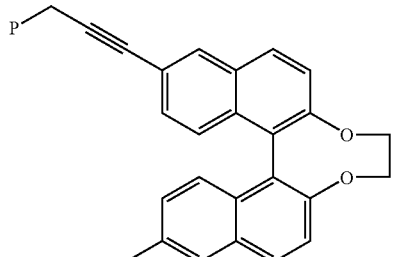
Ia1

Ia2

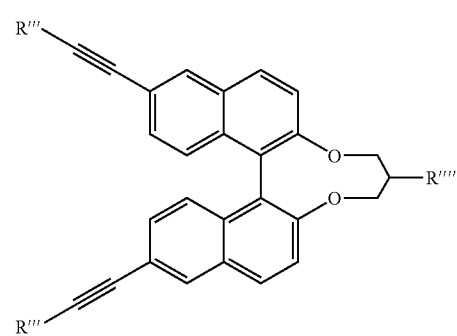
Ie

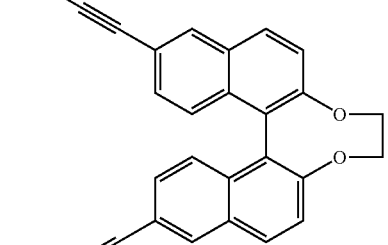
Ib1

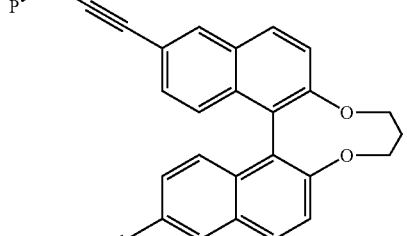
Ib2

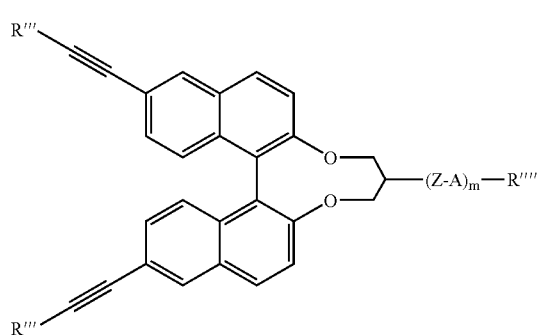
If

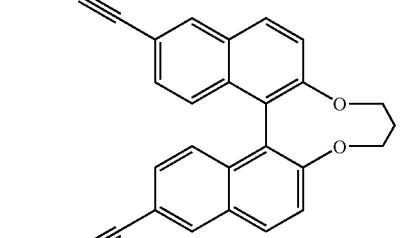
Ic1 wherein

R' and R" have one of the meanings of $R^1$ in formula I,

R''' is P-Sp, preferably P—$CH_2$—, or has one of the meanings of $R^1$ in formula I, R'''' is P-Sp or has one of the meanings of $R^1$ in formula I, Z has one of the meanings of $Z^1$ in formula I, A has one of the meanings of $A^1$ in formula I.

Especially preferred are compounds of the following sub-formulae

Ic2
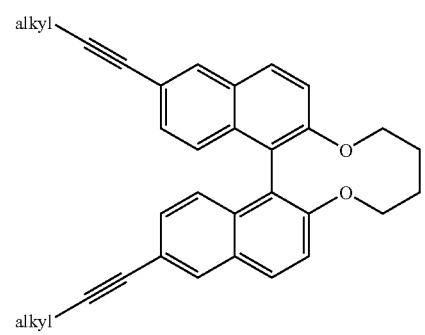
Id1
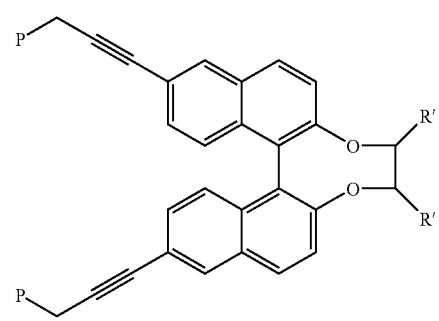
Id2
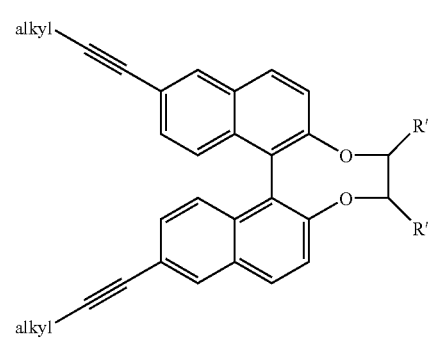
Ie1
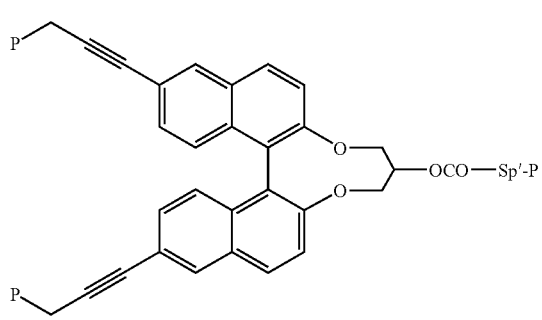
Ie2
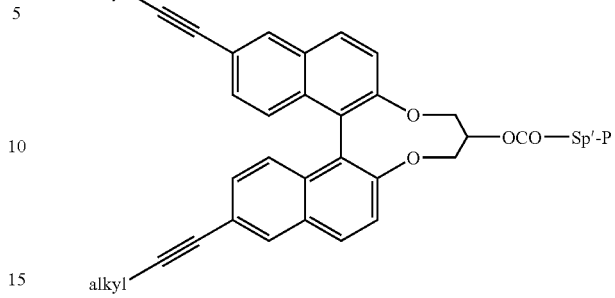
If1
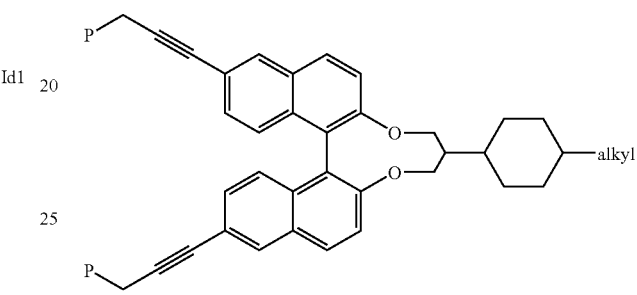
If2
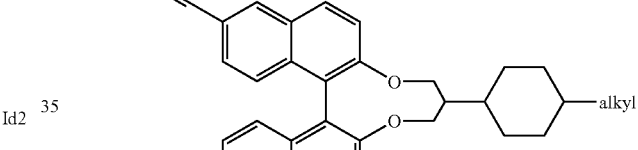
If3
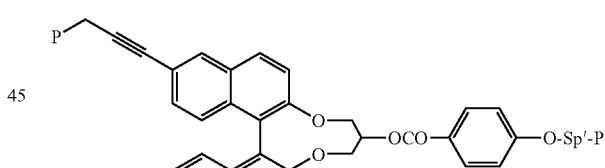
If4
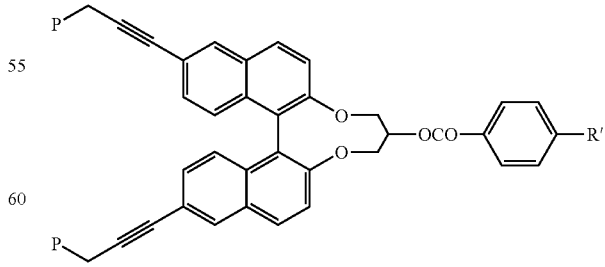
wherein R', P and Sp' are as defined above, and "alkyl" is n-alkyl with 1 to 12 C atoms, preferably methyl, ethyl, propyl, butyl, pentyl or hexyl.

The compounds of formula I can be synthesized according to or in analogy to methods which are known per se and which are described in the literature and in standard works of organic chemistry such as, for example, Houben-Weyl, Methoden der organischen Chemie, Thieme-Verlag, Stuttgart. Preferably the compounds are synthesized according to or in analogy to the methods shown in the examples.

According to a preferred method, Binaphthol is reacted with bromine in a suitable organic solvent, preferably dichloromethane, at low temperatures, preferably −70° C. The intermediate 6,6'-dibromo-[1,1']binaphthalenyl-2,2'-diol is reacted with an alkyl ditosylate and potassium carbonate in a suitable organic solvent, preferably NMP. The resulting ring closed intermediate is reacted with an aromatic acetylene compound in the presence of a base, preferably triethylamine, and a catalytic amount of a copper salt, preferably copper iodide, and a palladium catalyst, preferably bis(triphenylphosphine)dichloride, to form a desired product with high HTP. This is also depicted in the Schemes shown in the examples. The method to prepare a compound of formula I is another aspect of the invention.

The compounds of formula I can be used in LC mixtures for LCDs exhibiting a twisted structure like, for example, twisted or supertwisted nematic (TN, STN) displays with multiplex or active matrix addressing, or in cholesteic displays like surface stabilized or polymer stabilized cholestric texture displays (SSCT, PSCT) as described in WO 92/19695, WO 93/23496, U.S. Pat. No. 5,453,863 or U.S. Pat. No. 5,493,430, for LCDs with variable pitch, like multi-domain LCDs as described in WO 98/57223, multicolour cholesteric displays as described in U.S. Pat. No. 5,668,614, or displays comprising a chiral LC medium operating in the isotropic or blue phase as described in WO 02/93244.

The inventive compounds of formula I are also suitable for use in thermochromic or photochromic LC media, which change their colour upon temperature change or photoirradiation, respectively.

Thus, another aspect of the invention is an LC mixture comprising at least one chiral compound of formula I. Yet another aspect of the invention are cholesteric LCDs comprising cholesteric LC media containing at least one chiral compound of formula I.

The compounds of formula I have a good solubility in LC host mixtures, and can be added as dopants to LC hosts in high amounts without significantly affecting the phase behaviour and electrooptical properties of the mixture. Undesired spontaneous crystallization at low temperatures is thereby reduced and the operating temperature range of the mixture can be broadened. Furthermore, they can be used for the preparation of highly twisted LC media even if they have a low HTP, because the dopant concentration can be increased to yield low pitch values (i.e. high twist) without affecting the mixture properties. The use of a second dopant, which is often added to avoid crystallization, can thus be avoided. As the chiral compounds of formula I exhibit high HTP values, an LC mixture with high helical twist, i.e. a low pitch, can be prepared by adding these compounds in very small amounts.

Such an LC mixture comprises preferably 0.1 to 30%, in particular 1 to 25% and very particularly preferably 2 to 15% by weight of chiral compounds of formula I. Preferably it comprises 1 to 3 chiral compounds of formula I.

In a preferred embodiment of the invention the LC mixture is consisting of 2 to 25, preferably 3 to 15 compounds, at least one of which is a chiral compound of formula I. The other compounds are preferably low molecular weight LC compounds selected from nematic or nematogenic substances, for example from the known classes of the azoxybenzenes, benzylidene-anilines, biphenyls, terphenyls, phenyl or cyclohexyl benzoates, phenyl or cyclohexyl esters of cyclohehexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-biscyclohexylbenzenes, 4,4'-biscyclohexylbiphenyls, phenyl- or cyclohexylpyrimidines, phenyl- or cyclohexylpyridines, phenyl- or cyclohexylpyridazines, phenyl- or cyclohexyldioxanes, phenyl- or cyclohexyl-1,3-dithianes, 1,2-diphenyl-ethanes, 1,2-dicyclohexylethanes, 1-phenyl-2-cyclohexylethanes, 1-cyclohexyl-2-(4-phenylcyclohexyl)ethanes, 1-cyclohexyl-2-biphenylethanes, 1-phenyl2-cyclohexylphenylethanes, optionally halogenated stilbenes, benzyl phenyl ether, tolanes, substituted cinnamic acids and further classes of nematic or nematogenic substances. The 1,4-phenylene groups in these compounds may also be laterally mono- or difluorinated. The LC mixture is preferably based on achiral compounds of this type.

The most important compounds that can be used as components of the LC mixture can be characterized by the following formula

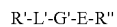

wherein L' and E, which may be identical or different, are in each case, independently from one another, a bivalent radical from the group formed by -Phe-, -Cyc-, -Phe-Phe-, -Phe-Cyc-, -Cyc-Cyc-, -Pyr-, -Dio-, —B-Phe- and —B-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl abd B is 2-(trans-1,4-cyclohexyl)ethyl, pyrimidine-2,5-diyl, pyridine-2,5-diyl or 1,3-dioxane-2,5-diyl.

G' in these compounds is selected from the following bivalent groups —CH═CH—, —N(O)N—, —CH═CY—, —CH═N(O)—, —C≡C—, —CH$_2$—CH$_2$—, —CO—O—, —CH$_2$—O—, —CO—S—, —CH$_2$—S—, —CH═N—, —COO-Phe-COO— or a single bond, with Y being halogen, preferably chlorine, or —CN.

R' and R" are, in each case, independently of one another, alkyl, alkenyl, alkoxy, alkenyloxy, alkanoyloxy, alkoxycarbonyl or alkoxycarbonyloxy with 1 to 18, preferably 3 to 12 C atoms, or alternatively one of R' and R" is F, CF$_3$, OCF$_3$, Cl, NCS or CN.

In most of these compounds R' and R" are, in each case, independently of each another, alkyl, alkenyl or alkoxy with different chain length, wherein the sum of C atoms in nematic media generally is between 2 and 9, preferably between 2 and 7.

Many of these compounds or mixtures thereof are commercially available. All of these compounds are either known or can be prepared by methods which are known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for said reactions. Use may also be made here of variants which are known per se, but are not mentioned here.

A preferred use of the compounds of formula I is the preparation of polymerizable LC mixtures, anisotropic polymer gels and anisotropic polymer films, in particular polymer films that exhibit a helically twisted molecular structure with uniform planar orientation, i.e. wherein the helical axis is oriented perpendicular to the plane of the film, like oriented cholesteric films.

Anisotropic polymer gels and displays comprising them are disclosed for example in DE 195 04 224 and GB 2 279 659.

Oriented cholesteric polymer films can be used for example as broadband reflective polarizers, colour filters, security markings, or for the preparation of LC pigments.

Thus, another aspect of the invention is a polymerizable LC material comprising one or more compounds of formula I and one or more further compounds, which can also be polymerizable and/or LC compounds.

The polymerizable LC material is preferably a mixture of two or more compounds, at least one of which is polymerizable or crosslinkable compound. Polymerizable compounds with one polymerizable group are hereinafter also referred to as "monoreactive". Crosslinkable compounds, i.e. having two or more polymerizable groups, are hereinafter also referred to as "di- or multireactive".

The polymerizable mesogenic or LC compounds are preferably monomers, very preferably calamitic monomers. These materials typically have good optical properties, like reduced chromaticity, and can be easily and quickly aligned into the desired orientation, which is especially important for the industrial production of polymer films at large scale. It is also possible that the polymerizable material comprises one or more discotic monomers.

The polymerizable materials as described above and below are another aspect of the invention.

Polymerizable mesogenic mono-, di- and multireactive compounds suitable for the present invention can be prepared by methods which are known per se and which are described in standard works of organic chemistry like for example Houben-Weyl, Methoden der organischen Chemie, Thieme-Verlag, Stuttgart.

Suitable polymerizable mesogenic or LC compounds for use as monomer or comonomer in a polymerizable LC mixture are disclosed for example in WO 93/22397, EP 0 261 712, DE 195 04 224, WO 95/22586, WO 97/00600, U.S. Pat. No. 5,518,652, U.S. Pat. No. 5,750,051, U.S. Pat. No. 5,770, 107 and U.S. Pat. No. 6,514,578.

Examples of suitable and preferred polymerizable mesogenic or LC compounds (reactive mesogens) are shown in the following list.

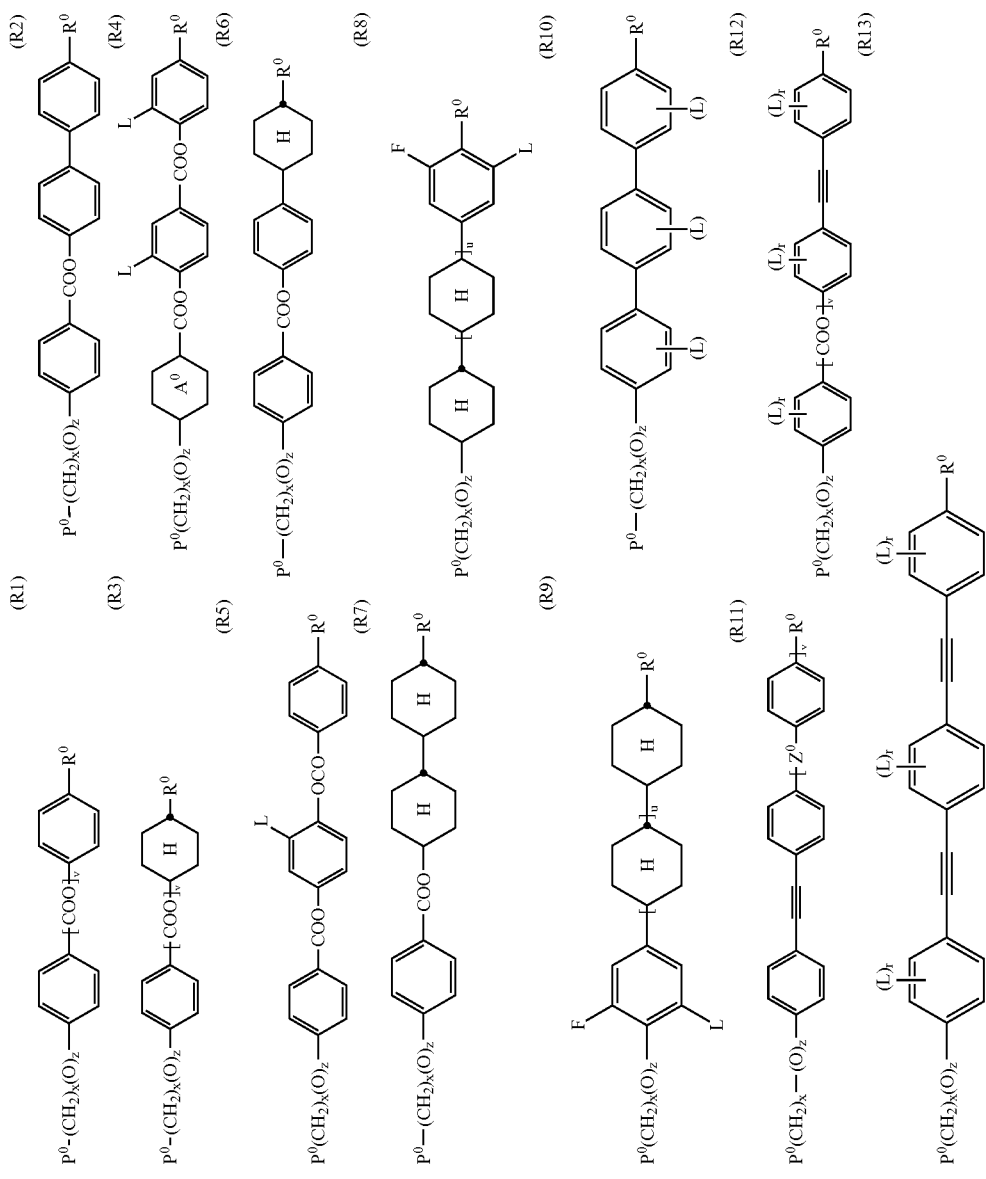

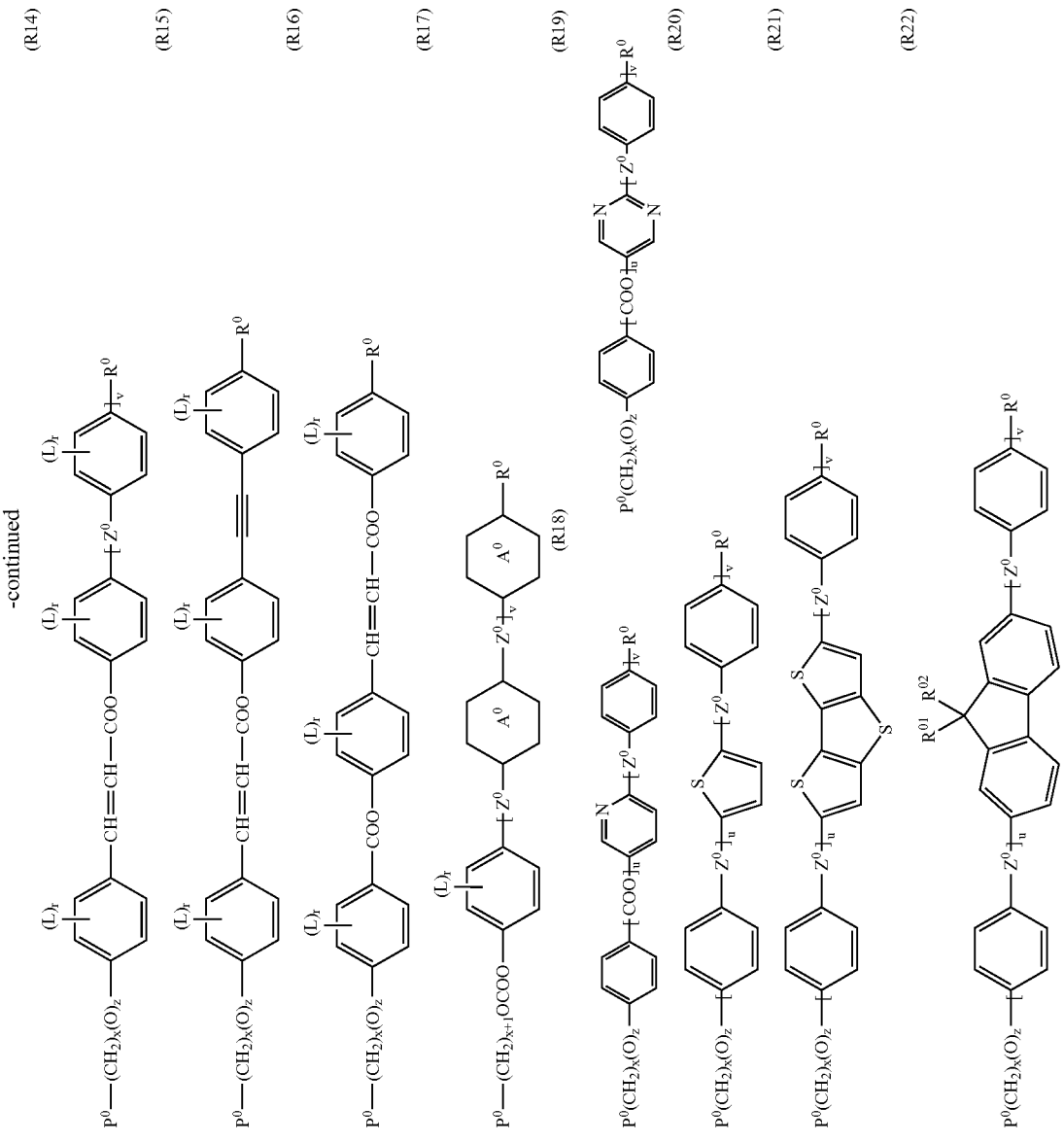

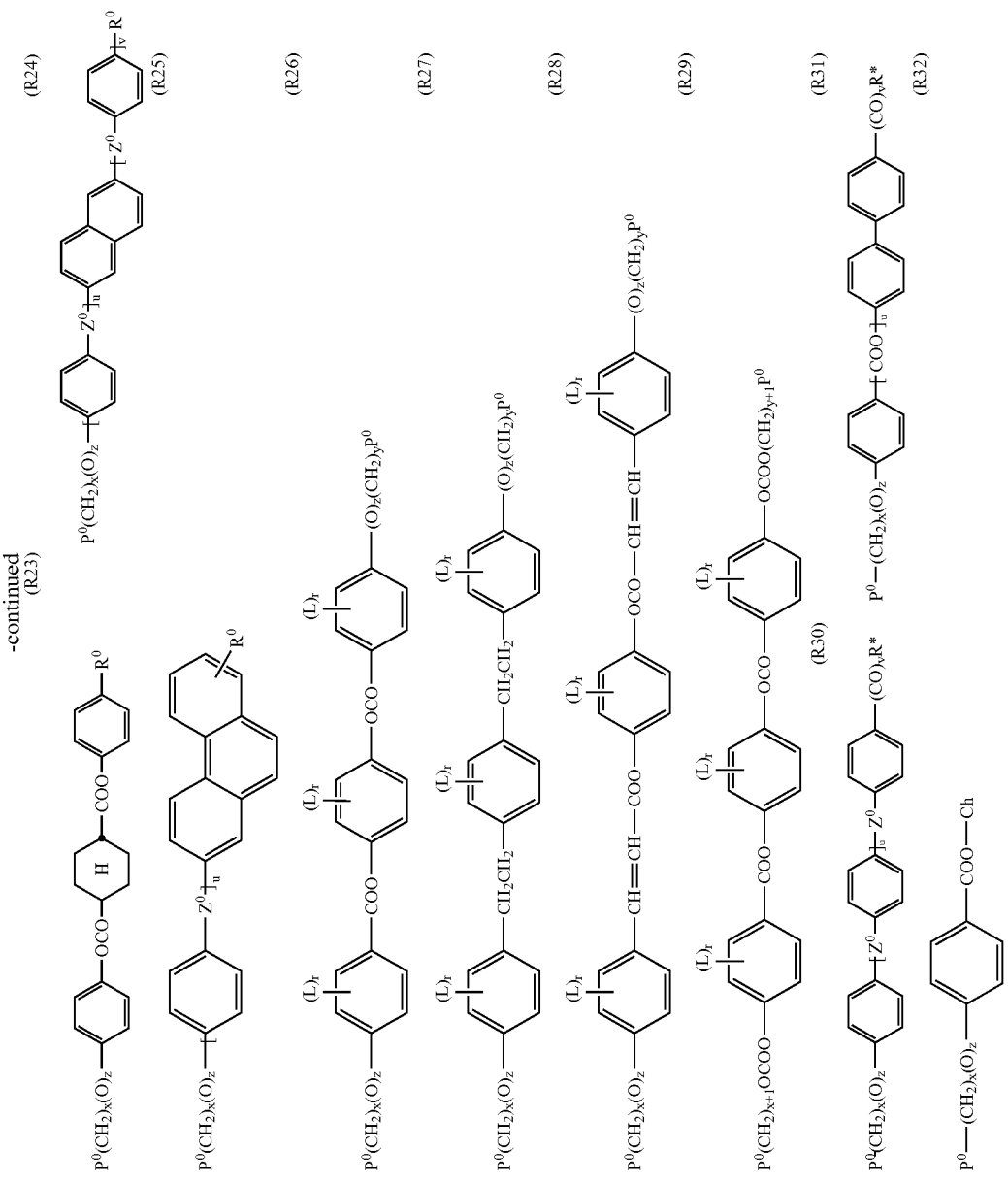

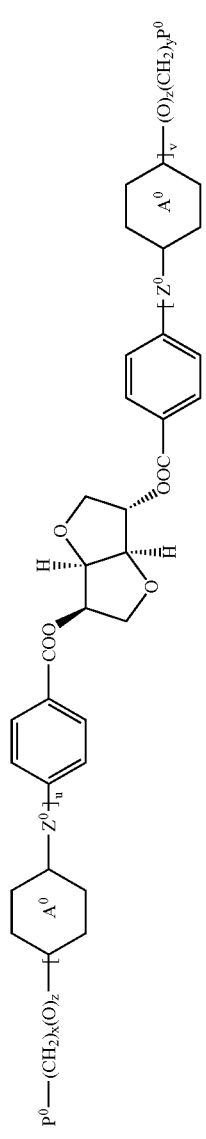
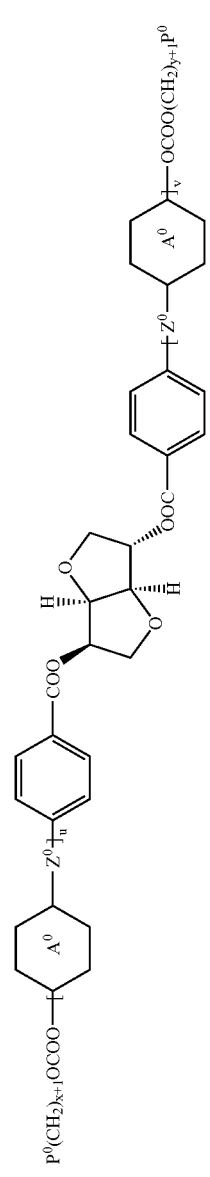
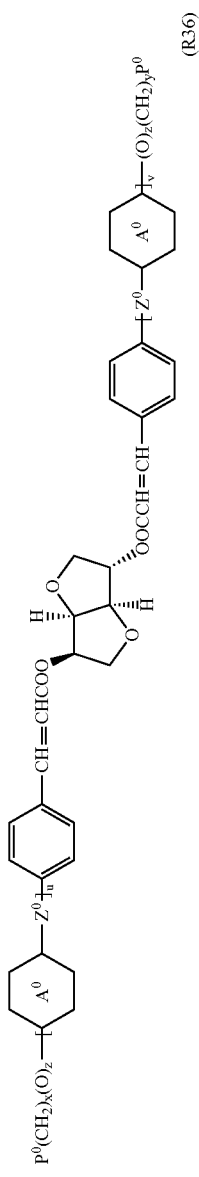
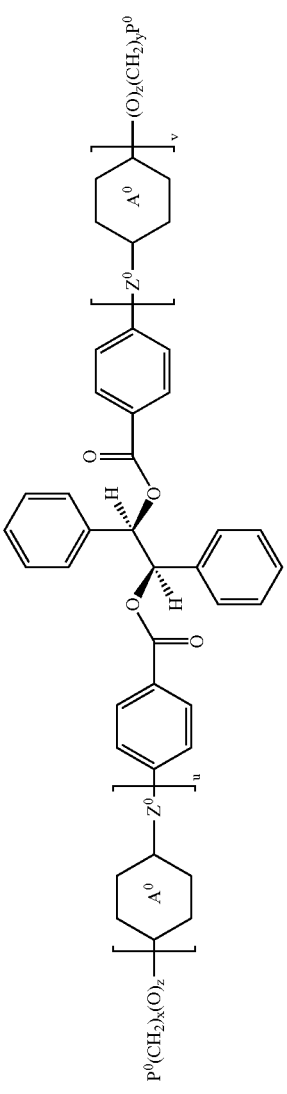

wherein

P⁰ is, in case of multiple occurrence independently of one another, a polymerizable group, preferably an acryl, methacryl, oxetane, epoxy, vinyl, vinyloxy, propenyl ether or styrene group, r is 0, 1, 2, 3 or 4, x and y are independently of each other 0 or identical or different integers from 1 to 12, z is 0 or 1, with z being 0 if the adjacent x or y is 0, A⁰ is, in case of multiple occurrence independently of one another, 1,4-phenylene that is optionally substituted with 1, 2, 3 or 4 groups L, or trans-1,4-cyclohexylene, u and v are independently of each other 0 or 1, Z⁰ is, in case of multiple occurrence independently of one another, —COO—, —OCO—, —CH$_2$CH$_2$—, —C≡C—, —CH=CH—, —CH=CH—COO—, —OCO—CH=CH— or a single bond, R⁰ is alkyl, alkoxy, thioalkyl, alkylcarbonyl, alkoxycarbonyl, alkylcarbonyloxy or alkoxycarbonyloxy with 1 or more, preferably 1 to 15 C atoms which is optionally fluorinated, or is Y⁰ or P—(CH$_2$)$_y$—(O)$_z$—, Y⁰ is F, Cl, CN, NO$_2$, OCH$_3$, OCN, SCN, SF$_5$, optionally fluorinated alkylcarbonyl, alkoxycarbonyl, alkylcarbonyloxy or alkoxycarbonyloxy with 1 to 4 C atoms, or mono- oligo- or polyfluorinated alkyl or alkoxy with 1 to 4 C atoms, R$^{01,02}$ are independently of each other H, R⁰ or Y⁰, R* is a chiral alkyl or alkoxy group with 4 or more, preferably 4 to 12 C atoms, like 2-methylbutyl, 2-methyloctyl, 2-methylbutoxy or 2-methyloctoxy, Ch is a chiral group selected from cholesteryl, estradiol, or terpenoid radicals like menthyl or citronellyl, L is, in case of multiple occurrence independently of one another, H, F, Cl, CN or optionally halogenated alkyl, alkoxy, alkylcarbonyl, alkoxycarbonyl, alkylcarbonyloxy or alkoxycarbonyloxy with 1 to 5 C atoms, and wherein the benzene rings can additionally be substituted with one or more identical or different groups L.

In addition to compounds of formula I, the polymerizable material may further comprise one or more polymerizable or unpolymerizable chiral compounds.

Suitable unpolymerizable chiral compounds are for example standard chiral dopants like R- or S-811, R- or S-1011, R- or S-2011, R- or S-3011, R- or S-4011, R- or S-5011, or CB 15 (all available from Merck KGaA, Darmstadt, Germany), sorbitols as described in WO 98/00428, hydrobenzoins as described in GB 2,328,207, chiral binaphthols as described in WO 02/94805, chiral binaphthol acetals as described in WO 02/34739, chiral TADDOLs as described in WO 02/06265, or chiral compounds having fluorinated linkage groups as described in WO 02/06196 or WO 02/06195. Suitable polymerizable chiral compounds are for example those listed above, or the polymerizable chiral material Paliocolor® LC756 (from BASF AG, Ludwigshafen, Germany).

The general preparation of polymer LC films according to this invention is known to the ordinary expert and described in the literature. Typically a polymerizable LC material is coated or otherwise applied onto a substrate where it aligns into uniform orientation, and polymerized in situ in its LC phase at a selected temperature for example by exposure to heat or actinic radiation, preferably by photo-polymerization, very preferably by UV-photopolymerization, to fix the alignment of the LC molecules. If necessary, uniform alignment can promoted by additional means like shearing or annealing the LC material, surface treatment of the substrate, or adding surfactants to the LC material.

As substrate for example glass or quarz sheets or plastic films can be used. It is also possible to put a second substrate on top of the coated material prior to and/or during and/or after polymerization. The substrates can be removed after polymerization or not. When using two substrates in case of curing by actinic radiation, at least one substrate has to be transmissive for the actinic radiation used for the polymerisation. Isotropic or birefringent substrates can be used. In case the substrate is not removed from the polymerized film after polymerisation, preferably isotropic substrates are used.

Suitable and preferred plastic substrates are for example films of polyester such as polyethyleneterephthalate (PET) or polyethylenenaphthalate (PEN), polyvinylalcohol (PVA), polycarbonate (PC) or triacetylcellulose (TAC), very preferably PET or TAC films. As birefringent substrates for example uniaxially stretched plastics film can be used. PET films are commercially available for example from DuPont Teijin Films under the trade name Melinex®).

The polymerizable material can be applied onto the substrate by conventional coating techniques like spin-coating or blade coating. It can also be applied to the substrate by conventional printing techniques which are known to the expert, like for example screen printing, offset printing, reel-to-reel printing, letter press printing, gravure printing, rotogravure printing, flexographic printing, intaglio printing, pad printing, heat-seal printing, ink-jet printing or printing by means of a stamp or printing plate.

It is also possible to dissolve the polymerizable material in a suitable solvent. This solution is then coated or printed onto the substrate, for example by spin-coating or printing or other known techniques, and the solvent is evaporated off before polymerization. In many cases it is suitable to heat the mixture in order to facilitate the evaporation of the solvent. As solvents for example standard organic solvents can be used. The solvents can be selected for example from ketones such as acetone, methyl ethyl ketone, methyl propyl ketone or cyclohexanone; acetates such as methyl, ethyl or butyl acetate or methyl acetoacetate; alcohols such as methanol, ethanol or isopropyl alcohol; aromatic solvents such as toluene or xylene; halogenated hydrocarbons such as di- or trichloromethane; glycols or their esters such as PGMEA (propyl glycol monomethyl ether acetate), γ-butyrolactone, and the like. It is also possible to use binary, ternary or higher mixtures of the above solvents.

Initial alignment (e.g. planar alignment) of the polymerizable LC material can be achieved for example by rubbing treatment of the substrate, by shearing the material during or after coating, by annealing the material before polymerization, by application of an alignment layer, by applying a magnetic or electric field to the coated material, or by the addition of surface-active compounds to the material. Reviews of alignment techniques are given for example by 1. Sage in "Thermotropic Liquid Crystals", edited by G. W. Gray, John Wiley & Sons, 1987, pages 75-77; and by T. Uchida and H. Seki in "Liquid Crystals—Applications and Uses Vol. 3", edited by B. Bahadur, World Scientific Publishing, Singapore 1992, pages 1-63. A review of alignment materials and techniques is given by J. Cognard, Mol. Cryst. Liq. Cryst. 78, Supplement 1 (1981), pages 1-77.

Especially preferred is a polymerizable material comprising one or more surfactants that promote a specific surface alignment of the LC molecules. Suitable surfactants are described for example in J. Cognard, Mol. Cryst. Liq. Cryst. 78, Supplement 1, 1-77 (1981). Preferred aligning agents for planar alignment are for example non-ionic surfactants, preferably fluorocarbon surfactants such as the commercially available Fluorad FC-171® (from 3M Co.) or Zonyl FSN® (from DuPont), multiblock surfactants as described in GB 2 383 040 or polymerizable surfactants as described in EP 1 256 617.

It is also possible to apply an alignment layer onto the substrate and provide the polymerizable material onto this alignment layer. Suitable alignment layers are known in the art, like for example rubbed polyimide or alignment layers prepared by photoalignment as described in U.S. Pat. No. 5,602,661, U.S. Pat. No. 5,389,698 or U.S. Pat. No. 6,717, 644.

It is also possible to induce or improve alignment by annealing the polymerizable LC material at elevated temperature, preferably at its polymerization temperature, prior to polymerization.

Polymerization is achieved for example by exposing the polymerizable material to heat or actinic radiation. Actinic radiation means irradiation with light, like UV light, IR light or visible light, irradiation with X-rays or gamma rays or irradiation with high energy particles, such as ions or electrons. Preferably polymerization is carried out by UV irradiation. As a source for actinic radiation for example a single UV lamp or a set of UV lamps can be used. When using a high lamp power the curing time can be reduced. Another possible source for actinic radiation is a laser, like for example a UV, IR or visible laser.

Polymerization is preferably carried out in the presence of an initiator absorbing at the wavelength of the actinic radiation. For example, when polymerizing by means of UV light, a photoinitiator can be used that decomposes under UV irradiation to produce free radicals or ions that start the polymerization reaction. For polymerizing acrylate or methacrylate groups preferably a radical photoinitiator is used. For polymerizing vinyl, epoxide or oxetane groups preferably a cationic photoinitiator is used. It is also possible to use a thermal polymerization initiator that decomposes when heated to produce free radicals or ions that start the polymerization. Typical radicalic photoinitiators are for example the commercially available Irgacure® or Darocure® (Ciba Geigy AG, Basel, Switzerland). A typical cationic photoinitiator is for example UVI 6974 (Union Carbide).

The polymerizable material may also comprise one or more stabilizers or inhibitors to prevent undesired spontaneous polymerization, like for example the commercially available Irganox® (Ciba Geigy AG, Basel, Switzerland).

The curing time depends, inter alia, on the reactivity of the polymerizable material, the thickness of the coated layer, the type of polymerization initiator and the power of the UV lamp. The curing time is preferably $\leq 5$ minutes, very preferably $\leq 3$ minutes, most preferably $\leq 1$ minute. For mass production short curing times of $\leq 30$ seconds are preferred.

Preferably polymerization is carried out in an inert gas atmosphere like nitrogen or argon.

The polymerizable material may also comprise one or more dyes having an absorption maximum adjusted to the wavelength of the radiation used for polymerization, in particular UV dyes like e.g. 4,4"-azoxy anisole or Tinuvin® dyes (from Ciba AG, Basel, Switzerland).

In another preferred embodiment the polymerizable material comprises one or more monoreactive polymerizable non-mesogenic compounds, preferably in an amount of 0 to 50%, very preferably 0 to 20%. Typical examples are alkylacrylates or alkylmethacrylates.

In another preferred embodiment the polymerizable material comprises one or more di- or multireactive polymerizable non-mesogenic compounds, preferably in an amount of 0 to 50%, very preferably 0 to 20%, alternatively or in addition to the di- or multireactive polymerizable mesogenic compounds. Typical examples of direactive non-mesogenic compounds are alkyldiacrylates or alkyldimethacrylates with alkyl groups of 1 to 20 C atoms. Typical examples of multireactive non-mesogenic compounds are trimethylpropanetrimethacrylate or pentaeryth ritoltetraacrylate.

It is also possible to add one or more chain transfer agents to the polymerizable material in order to modify the physical properties of the polymer film. Especially preferred are thiol compounds, for example monofunctional thiols like dodecane thiol or multifunctional thiols like trimethylpropane tri (3-mercaptopropionate). Very preferred are mesogenic or LC thiols as disclosed for example in WO 96/12209, WO 96/25470 or U.S. Pat. No. 6,420,001. By using chain transfer agents the length of the free polymer chains and/or the length of the polymer chains between two crosslinks in the polymer film can be controlled. When the amount of the chain transfer agent is increased, the polymer chain length in the polymer film decreases.

The polymerizable material may also comprise a polymeric binder or one or more monomers capable of forming a polymeric binder, and/or one or more dispersion auxiliaries. Suitable binders and dispersion auxiliaries are disclosed for example in WO 96/02597. Preferably, however, the polymerizable material does not contain a binder or dispersion auxiliary.

The polymerizable material can additionally comprise one or more additional components like for example catalysts, sensitizers, stabilizers, inhibitors, chain-transfer agents, co-reacting monomers, surface-active compounds, lubricating agents, wetting agents, dispersing agents, hydrophobing agents, adhesive agents, flow improvers, defoaming agents, deaerators, diluents, reactive diluents, auxiliaries, colourants, dyes or pigments.

The thickness of a polymer film according to the present invention is preferably from 0.3 to 5 microns, very preferably from 0.5 to 3 microns, most preferably from 0.7 to 1.5 microns. For use as alignment layer, thin films with a thickness of 0.05 to 1, preferably 0.1 to 0.4 microns are preferred.

The polymer film of the present invention can be used as retardation or compensation film for example in LCDs to improve the contrast and brightness at large viewing angles and reduce the chromaticity. It can be used outside the switchable LC cell of the LCD or between the substrates, usually glass substrates, forming the switchable LC cell and containing the switchable LC medium (incell application).

The polymer film of the present invention can also be used as alignment layer for LC materials. For example, it can be used in an LCD to induce or improve alignment of the switchable LC medium, or to align a subsequent layer of polymerizable LC material coated thereon. In this way, stacks of polymerized LC films can be prepared.

In particular, the chiral compounds, mixtures, polymers and polymer films according to the present invention can be used in reflective polarizers as disclosed in GB 2 315 072 or WO 97/35219, negative C plate retarders as disclosed in WO 01/20394 or WO 2004/013666, biaxial negative C plate retarders as disclosed in WO 2003/054111, alignment layers as disclosed in EP 1 376 163, birefringent markings or images for decorative or security use as disclosed in GB 2 315 760, WO 02/85642, EP 1 295 929 or EP 1 381 022.

The polymer film of the present invention can be used in conventional LC displays, for example displays with vertical alignment like the DAP (deformation of aligned phases), ECB (electrically controlled birefringence), CSH (colour super homeotropic), VA (vertically aligned), VAN or VAC (vertically aligned nematic or cholesteric), MVA (multi-domain vertically aligned) or PVA (patterned vertically aligned) mode; displays with bend or hybrid alignment like the OCB (optically compensated bend cell or optically compensated birefringence), R—OCB (reflective OCB), HAN (hybrid aligned nematic) or pi-cell (π-cell) mode; displays with twisted alignment like the TN (twisted nematic), HTN (highly twisted nematic), STN (super twisted nematic), AMD-TN (active matrix driven TN) mode; displays of the IPS (in plane switching) mode, or displays with switching in an optically isotropic phase or in the blue phase, as described for example in WO 02/93244.

Especially preferred are TN, STN, VA and IPS displays, in particular those of the active-matrix type. Further preferred are transflective displays.

In the foregoing and the following, all temperatures are given in degrees Celsius, and all percentages are by weight, unless stated otherwise. The following abbreviations are used to illustrate the LC phase behaviour: C, K=crystalline; N=nematic; S=smectic; N*, Ch=chiral nematic or cholesteric; I=isotropic. The numbers between these symbols indicate the phase transition temperatures in degree Celsius. Furthermore, mp is the melting point and cp is the clearing point (in ° C.).

Unless stated otherwise, the precentages of components of a polymerizable mixture as given above and below refer to the total amount of solids in the mixture polymerizable mixture, i.e. not including solvents.

The HTP of a chiral dopant in an LC host material is given as HTP=$(p \cdot c)^{-1}$ (in $\mu m^{-1}$), wherein p is the pitch of the molecular helix (in μm) and c is the concentration (in wt. %) of the chiral compound in the host (a concentration of 1% by weight for example corresponds to c=0.01). Unless stated otherwise, specific HTP values given above and below relate to a dopant concentration of 1% in the LC host mixture MLC-6260 (Merck KGaA, Darmstadt, Germany) at 20° C.

The examples below shall illustrate the invention without limiting it. The corresponding S,S- or R,R-isomers of all binaphthyl compounds shown in the examples can also be prepared according or in analogy to the methods described.

EXAMPLE 1

Compound (1) is prepared according to reaction scheme 1 below.

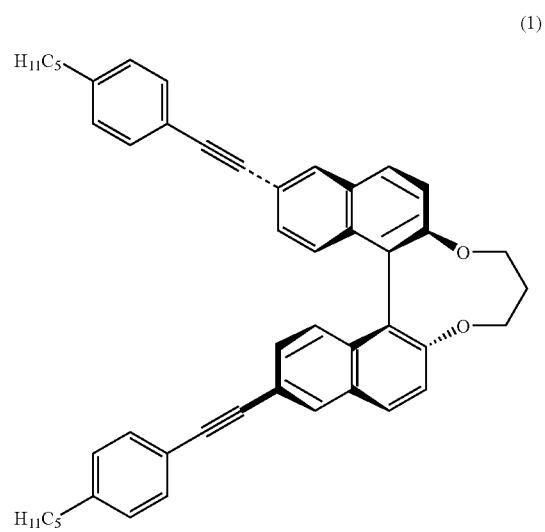

(1)

Scheme 1:

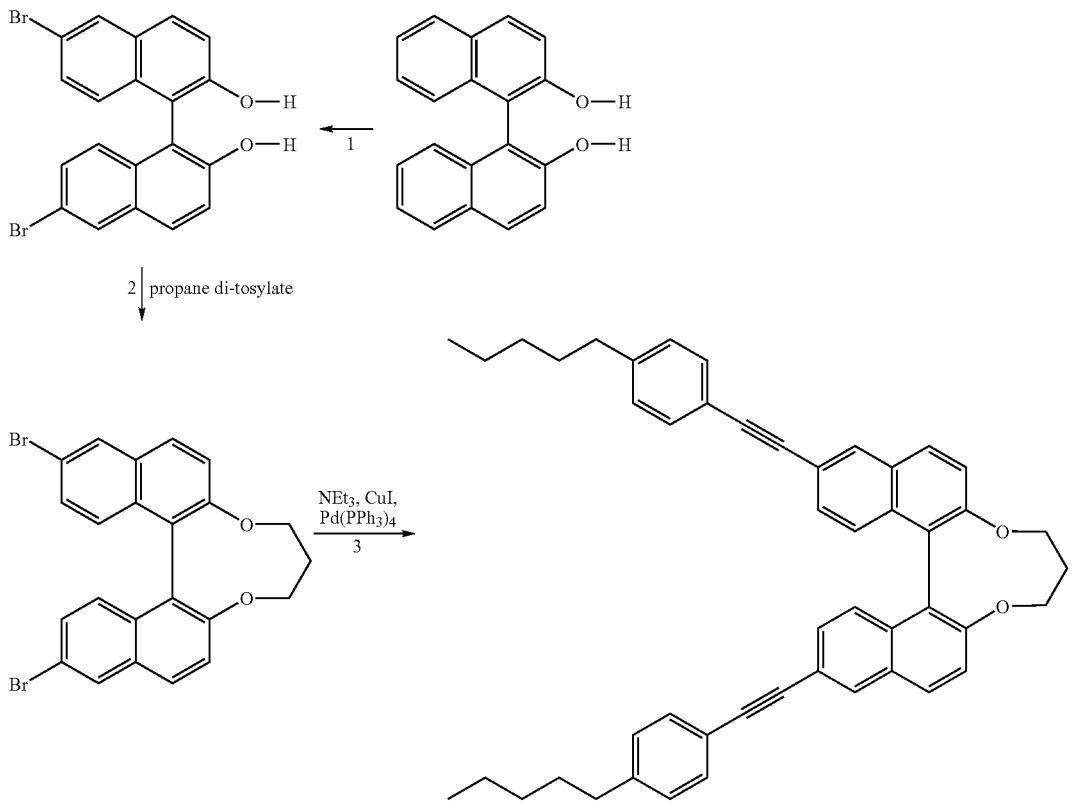

Step 1: S-(−)-6,6'-Dibromo-[1,1']binaphthalenyl-2,2'-diol

Bromine (10.2 ml, 200.0 mmol) is added dropwise to a solution of S-(−)-1,1'-bi-2-naphthol (30.0 g, 104.8 mmol) dissolved in dichloromethane (400 ml) at −70° C. under an atmosphere of nitrogen. The mixture is allowed to warm to room temperature, whereupon sodium bisulphite is added to destroy excess bromine. The solution is washed with brine, removed, dried over sodium sulphate and evaporated to dryness. The resulting crude product is recrystallised from a mixture of toluene and petrol to yield white crystals of the desired product. $^1$H NMR shows expected signals.

Step 2: S-(−)-6,6'-Dibromo-[1,1']binaphthalenyl-2,2'-dioxypropane

S-(−)-6,6'-Dibromo-[1,1']binaphthalenyl-2,2'-diol (10.0 g, 22.5 mmol), potassium carbonate (8.7 g, 62.6 mmol) and propane di-tosylate (8.7 g, 22.5 mmol) are stirred at 80° C. in NMP. After 16 hours the mixture is poured into ether and washed with water. The ethereal layer is removed, dried over sodium sulphate and evaporated to dryness. The resulting crude solid is purified by flash column chromatography using petrol/ethyl acetate (4/1) as eluant to yield white crystal of the desired product. $^1$H NMR shows expected signals.

Step 3: S-(−)-6,6'-bis[1-ethynyl-4-pentylbenzene]binaphthalenyl-2,2'-dioxypropane S-(−)-6,6'-Dibromo-[1,1']binaphthalenyl-2,2'-dioxypropane (1.0 g, 2.1 mmol), 1-ethyneyl-4-pentylbenzene (0.7 g, 4.1 mmol), triethylamine (5 mol), tetrahydrofuran (10 ml) and a catalytic amount of palladium bis(triphenylphosphine) dichloride and copper (1) iodide are stirred under reflux for 20 hours. The mixture is poured into dichloromethane, washed with water, dried over sodium sulphate and evaporated to dryness to leave a brown solid. Purification is achieved by flash column chromatography using dichloromethane/petrol as eluant to give upon evaporation of the appropriate fractions a white solid of the desired product. $^1$H and $^{13}$C NMR show expected signals. Optical microscopy shows a transition of K-47-I.

The helical twisting power (HTP) is extrapolated by dissolving 5 weight % of the compound in BL087 (from Merck Chemicals Ltd, UK). The HTP is 48, with a right handed twist sense.

EXAMPLE 2

Compound (2) is prepared according to reaction scheme 2 below.

(2)

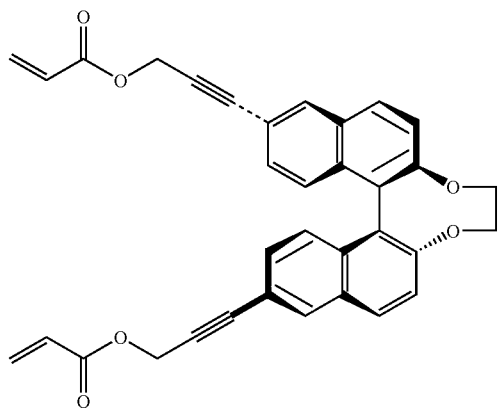

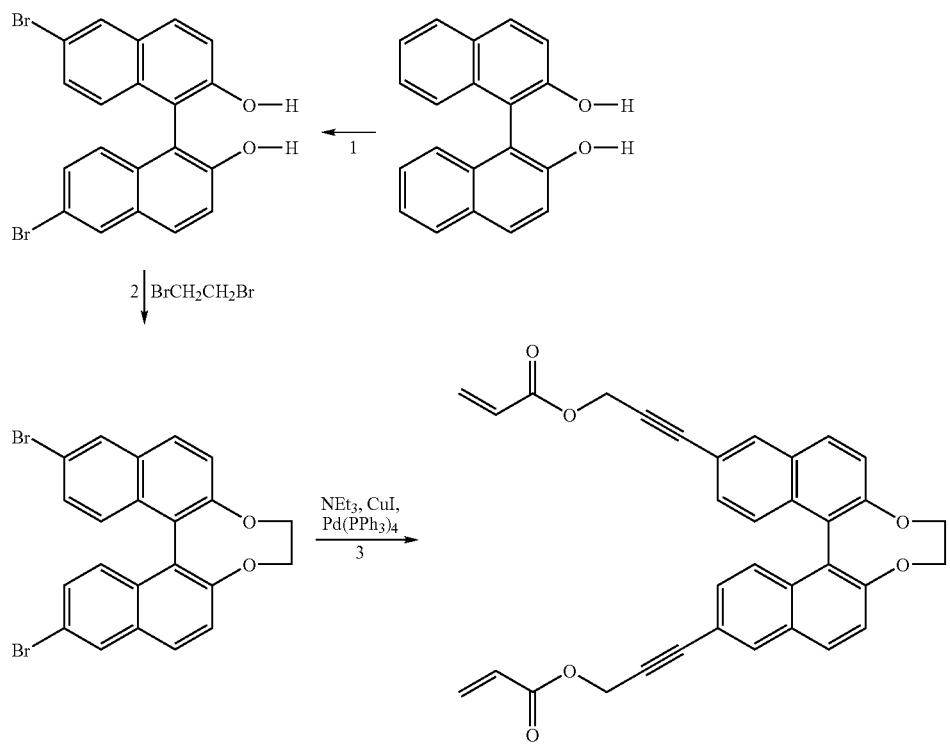

Scheme 2:

Step 1: Add bromine (2 equiv) to binaphthol in dichloromethane at −70° C., allow to warm to room temperature. Remove excess bromine by washing with sodium bisulphite and water, then dry. Recrystallise from toluene/petrol.

Step 2: Ring closure is achieved by stirring 1,2-dibromoethane (2.9 equiv), potassium carbonate (6 equiv.) and a catalytic amount of sodium iodide under reflux in acetone.

Step 3: Cross-coupling with acetylene compound is achieved under typical Sonogashira cross-coupling conditions, using triethylamine as a base, a catalytic amount of palladium tetrakistriphenylphoshine and copper (1) iodide in tetrahydrofuran as solvent.

EXAMPLE 3

Compound (3) is prepared according to reaction scheme 3 below.

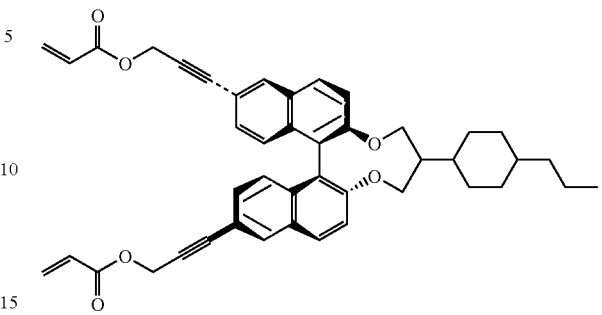

(3)

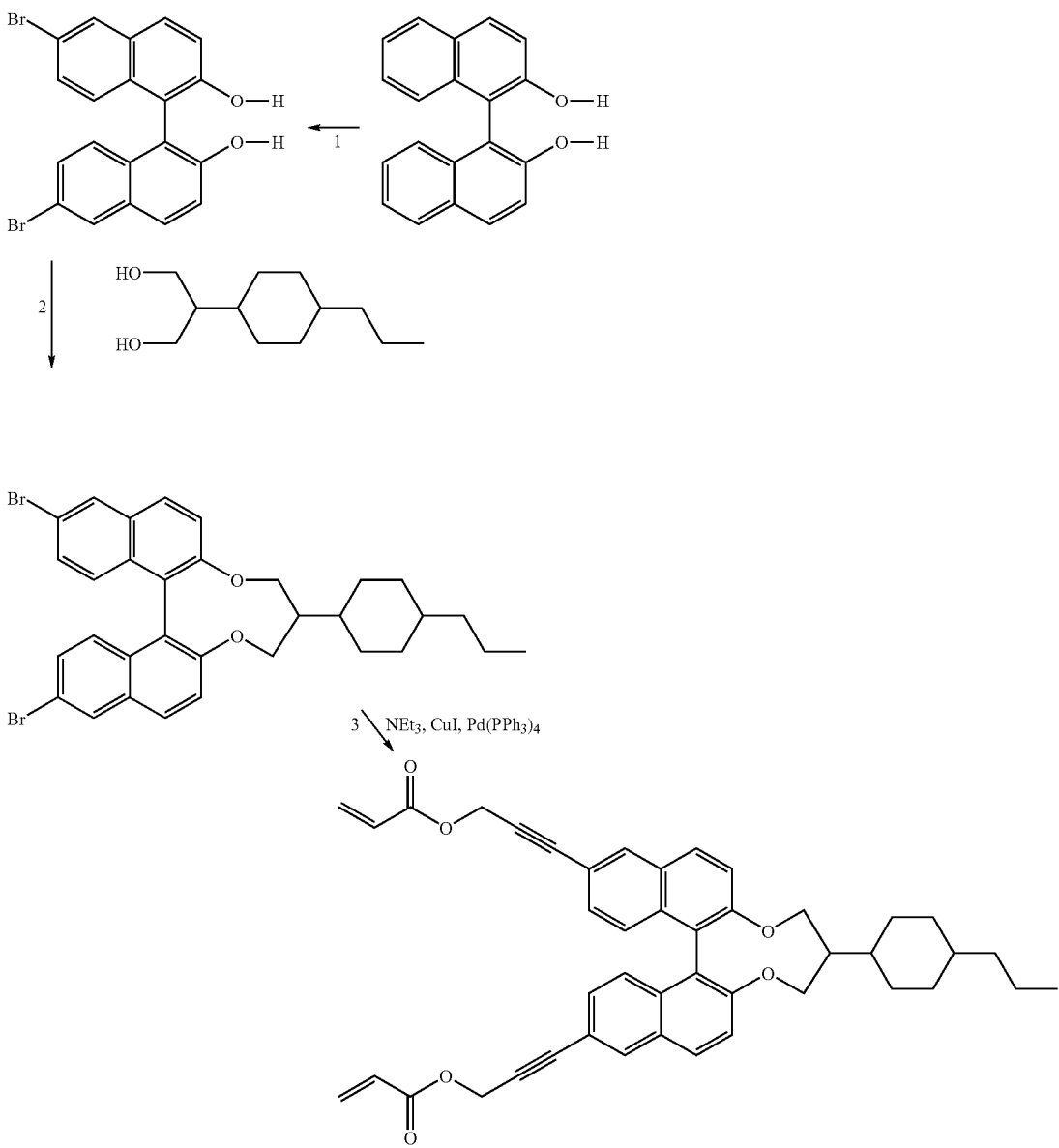

Step 1: Add bromine (2 equiv) to binaphthol in dichloromethane at −70° C., allow to warm to room temperature. Remove excess bromine by washing with sodium bisulphite and water, then dry. Recrystallise from toluene/petrol.

Step 2: Ring closure is achieved by Mitsunobu conditions, triphenylphosphine (2.3 equiv.), diisopropylazodicarboxylate (2.7 equiv.) in tetrahydrofuran at room temperature.

Step 3: Cross-coupling with acetylene compound is achieved under typical Sonogashira cross-coupling conditions, using triethylamine as a base, a catalytic amount of palladium tetrakistriphenylphoshine and copper (1) iodide in tetrahydrofuran as solvent.

EXAMPLE 4

Compound (4) is prepared according to reaction scheme 4 below.

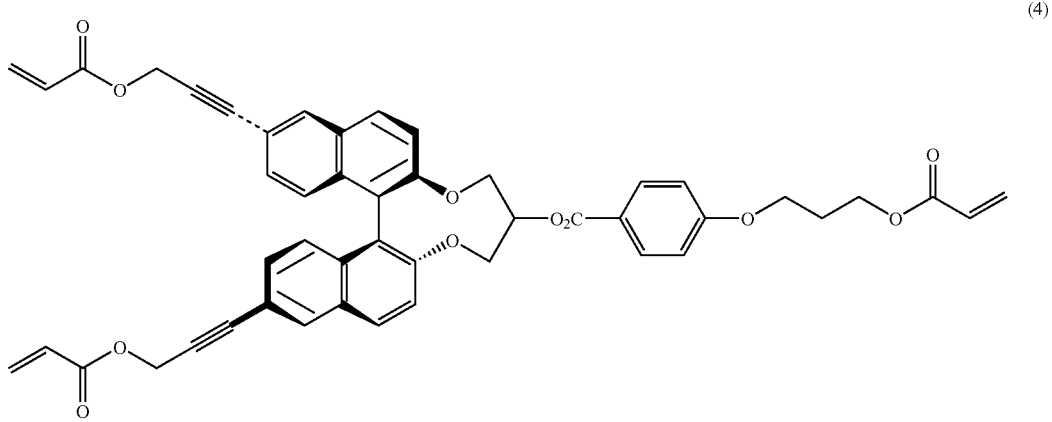

(4)

Scheme 4:

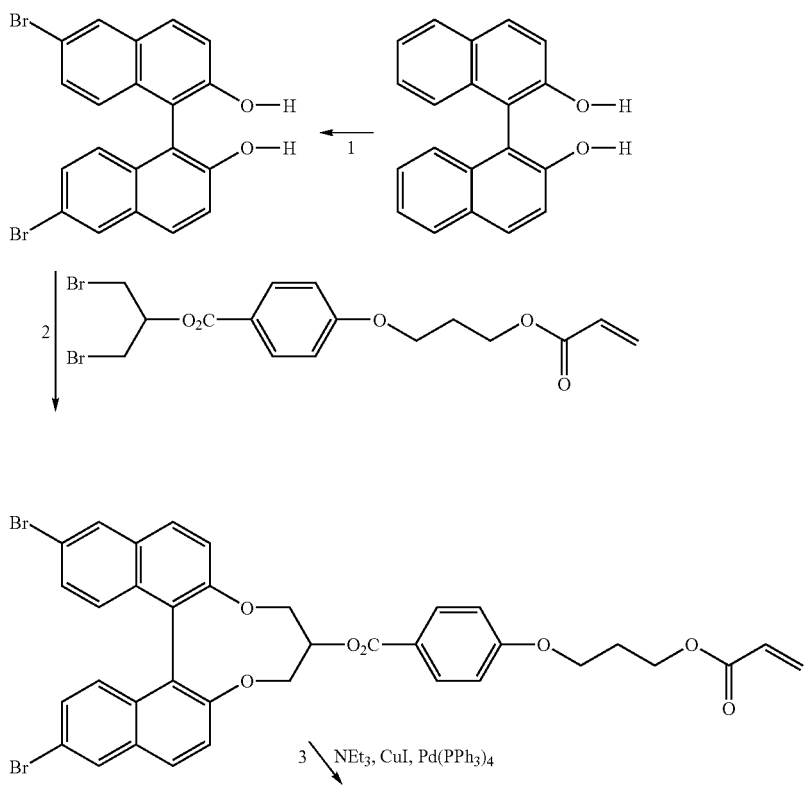

-continued

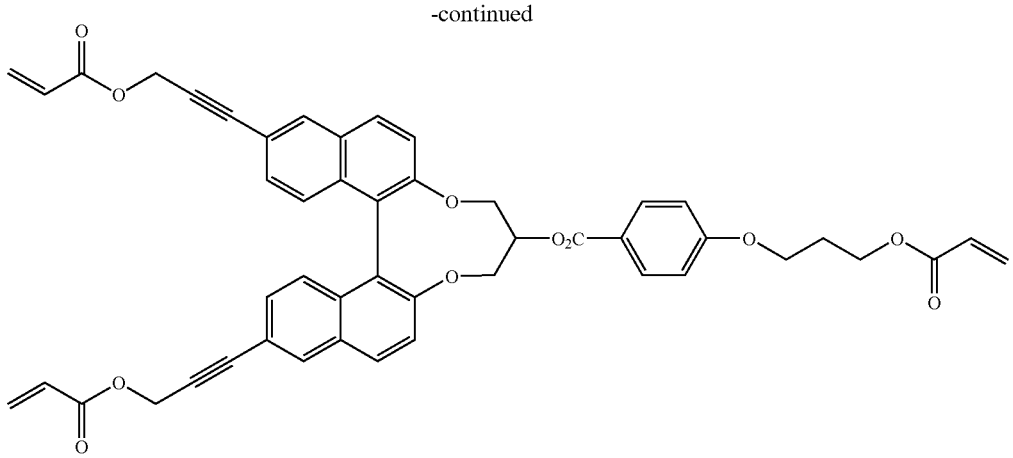

Step 1: Add bromine (2 equiv) to binaphthol in dichloromethane at −70° C., allow to warm to room temperature. Remove excess bromine by washing with sodium bisulphite and water, then dry. Recrystallise from toluene/petrol.

Step 2: Ring closure is achieved by etherification conditions, potassium carbonate, dimethyl formamide (90° C.) with 1,3-dibromo compound.

Step 3: Cross-coupling with acetylene compound is achieved under typical Sonogashira cross-coupling conditions, using triethylamine as a base, a catalytic amount of palladium tetrakistriphenylphoshine and copper (1) iodide in tetrahydrofuran as solvent.

EXAMPLE 5

Compound (5) is prepared as described below.

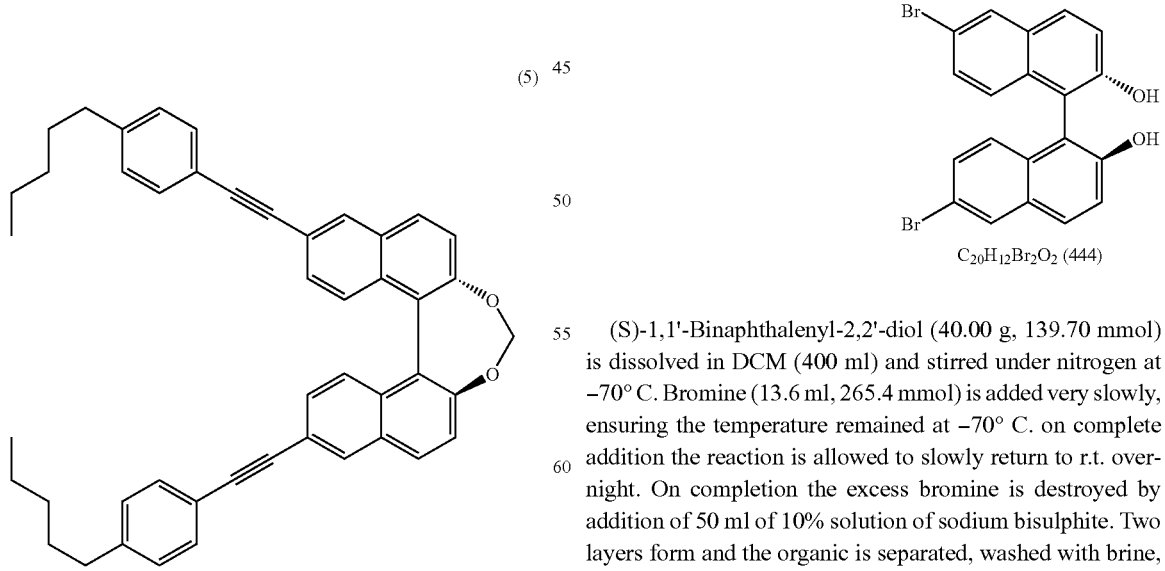

(S)-6,6'-Dibromo-1,1'-binaphthalenyl-2,2'-diol

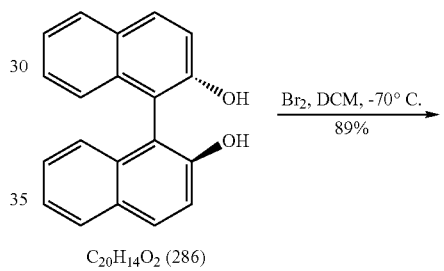

(S)-1,1'-Binaphthalenyl-2,2'-diol (40.00 g, 139.70 mmol) is dissolved in DCM (400 ml) and stirred under nitrogen at −70° C. Bromine (13.6 ml, 265.4 mmol) is added very slowly, ensuring the temperature remained at −70° C. on complete addition the reaction is allowed to slowly return to r.t. overnight. On completion the excess bromine is destroyed by addition of 50 ml of 10% solution of sodium bisulphite. Two layers form and the organic is separated, washed with brine, dried (sodium sulphate) and excess solvents removed in vacuo. The resulting solid is recrystallised from toluene/petrol to yield a white solid, which is dried without heating (55.2 g, 124.3 mmol, 89%). M.p. 79° C. $^1$H NMR and $^{13}$C NMR give expected signals. GCMS shows the (M/z) 444 ([M]$^+$.

(S)-9,14-Dibromodinaphtho[2,1-d:1',2'-f][1,3]dioxepine (S)-10,15-Dibromo-4,5-dihydrodinaphtho[2,1-e:1',2'-g][1,4]dioxocine

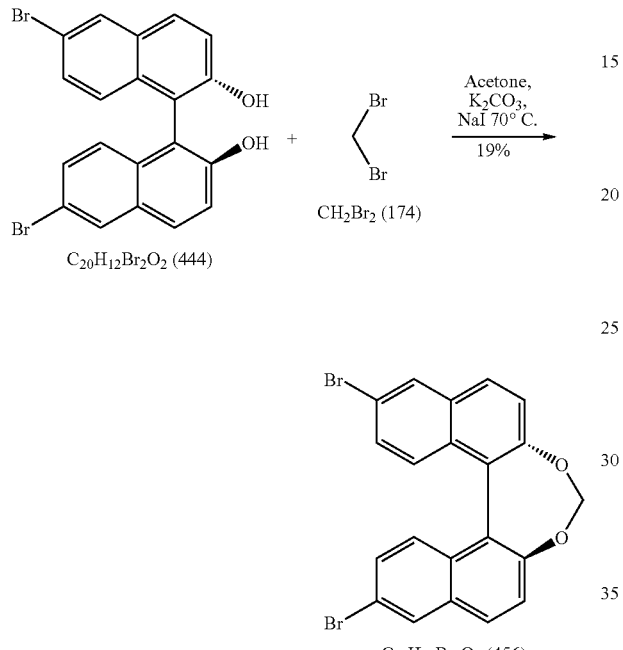

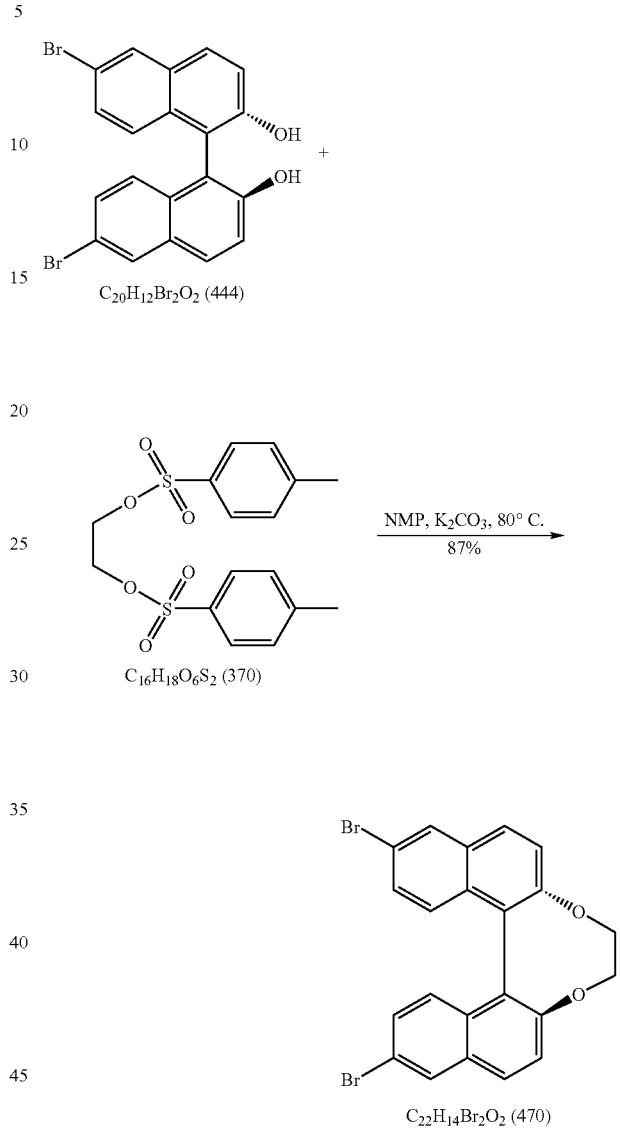

(S)-6,6'-Dibromo-1,1'-binaphthalenyl-2,2'-diol (5.00 g, 11.26 mmol) is dissolved in acetone (60 ml), potassium carbonate (9.80 g, 70.93 mmol) and sodium iodide (0.10 g, 0.67 mmol) are added and the resulting solution stirred at 70° C. Dibromomethane (5.68 ml, 32.65 mmol) in acetone (20 ml) is added slowly and the reaction stirred overnight. On completion the reaction is diluted with diethyl ether and poured onto water. The layers are separated and the aqueous phase extracted with diethyl ether (×2). Combined organic phases are washed with water (×2), dried over magnesium sulphate and excess solvents removed in vacuo to yield the product as a cream solid. The crude product is purified by FlashMaster column chromatography (SiO$_2$, 10% EtOAc/petrol) and a front running impurity is removed. The product is further purified by recrystallisation from the minimum amount of DCM in hot petrol the yield the product as off-white crystals (2.29 g). The product is further purified by preparative HPLC (100 ml/min, 30% water in acetonitrile running up to 100% acetonitrile after 8 minutes) to yield a white solid (0.99 g, 2.17 mmol, 19%).

M.p. 215° C. $^1$H NMR and $^{13}$C NMR give expected signals. GCMS shows the (M/z) 456 ([M]$^{+HTP=}$49 (5% concentration in BLO87, give a right handed twist).

(S)-6,6'-Dibromo-1,1'-binaphthalenyl-2,2'-diol (27.18 g, 61.20 mmol) is dissolved in NMP (150 ml), potassium carbonate (10.15 g, 73.44 mmol) is added and the resulting solution stirred at 80° C. Ethylene glycol di-p-tosylate (22.67 g, 61.20 mmol) in NMP (100 ml) is added slowly and the reaction stirred overnight. On completion the reaction is diluted with diethyl ether and poured onto water. Layers are separated and extracted once with diethyl ether. Combined organic phases are washed with water (×4), dried over magnesium sulphate and excess solvents removed in vacuo to yield the product as a brown solid. The solid is purified by column chromatography (SiO$_2$, 100% petrol, running up to 20% ethyl acetate/petrol) to yield compound 12 as white crystals (25.00 g, 53.19 mmol, 87%). M.p. 116° C. $^1$H NMR and $^{13}$C NMR give expected signals. GCMS shows the (M/z) 470 ([M]$^+$. HTP 47 (5% concentration in BLO87, give a right handed twist).

43

(S)-2,7-Dibromo-13,14-dihydro-12H-dinaphtho[2,1-f:1',2'-h][1,5]-dioxonine

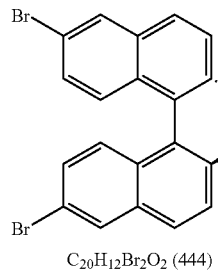

C$_{20}$H$_{12}$Br$_2$O$_2$ (444)

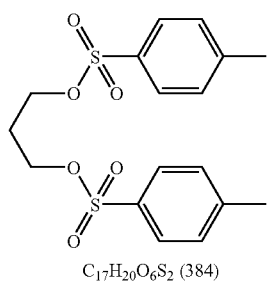

C$_{17}$H$_{20}$O$_6$S$_2$ (384)

NMP, K$_2$CO$_3$, 80° C.
63%

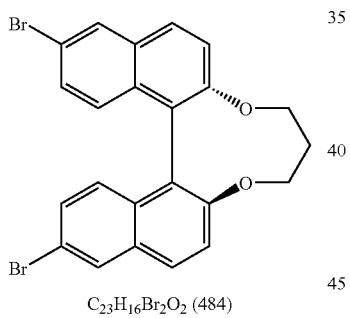

C$_{23}$H$_{16}$Br$_2$O$_2$ (484)

(S)-6,6'-Dibromo-1,1'-binaphthalenyl-2,2'-diol (90% content, 53.27 g, 107.94 mmol) is dissolved in NMP (150 ml), potassium carbonate (49.80 g, 129.53 mmol) is added and the resulting solution stirred at 80° C. Propane di-p-tosylate (41.50 g, 107.94 mmol) in NMP (400 ml) is added slowly and the reaction stirred overnight. On completion the reaction is diluted with diethyl ether and poured onto water. The layers are separated and the aqueous phase is extracted with diethyl ether (×2). Combined organic phases are washed with water (×3), dried over magnesium sulphate and excess solvents removed in vacuo to yield the product as a cream solid. The solid is purified by column chromatography (SiO$_2$, 100% petrol, running up to 20% ethyl acetate/petrol) to yield white crystals (32.64 g, 67.44 mmol, 63%). M.p. 179° C. $^1$H NMR and $^{13}$C NMR give expected signals. GCMS shows the (M/z) 484([M]$^+$. HTP=44 (5% concentration in BLO87, give a right handed twist).

44

(S)-2,7-Dibromo-12,13,14,15-tetrahydrodinaphtho[2,1-b:1',2'-d][1,6]dioxecine

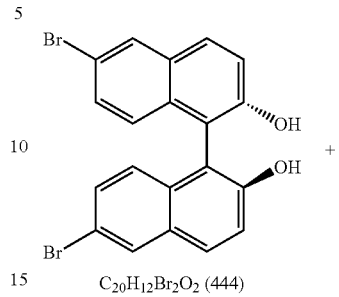

C$_{20}$H$_{12}$Br$_2$O$_2$ (444)

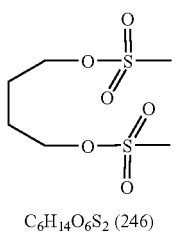

C$_6$H$_{14}$O$_6$S$_2$ (246)

NMP, K$_2$CO$_3$, 80° C.
57%

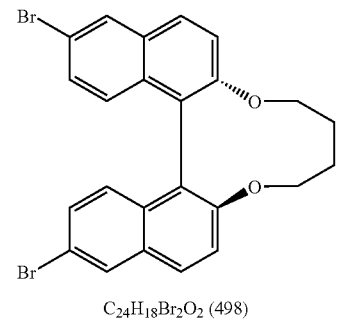

C$_{24}$H$_{18}$Br$_2$O$_2$ (498)

(S)-6,6'-Dibromo-1,1'-binaphthalenyl-2,2'-diol (5.00 g, 11.26 mmol) is dissolved in NMP (40 ml), potassium carbonate (1.87 g, 13.51 mmol) is added and the resulting solution stirred at 80° C. 1,4-butanediol dimethanesulfonate (2.77 g, 11.26 mmol) in NMP (40 ml) is added slowly and the reaction stirred overnight, after which NMP (80 ml) and potassium carbonate (1.87 g, 13.51 mmol) are added to dissolve a gel that had formed. On completion the reaction is diluted with diethyl ether and poured onto water. Layers are separated and extracted with diethyl ether (×2). Combined organic phases are washed with water (×3), dried over sodium sulphate and excess solvents removed in vacuo to yield the product as a cream solid. The solid is purified by column chromatography (SiO$_2$, 50% toluene/petrol) to yield compound 14 as an off-white solid (3.20 g, 6.42 mmol, 57%).

M.p. 109° C. $^1$H NMR and $^{13}$C NMR give expected signals. GCMS shows the (M/z) 498 ([M]$^+$. HTP=37 (7% concentration in BLO87, give a right handed twist).

(S)-9,14-bis((4-pentylphenyl)ethynyl)dinaphtho[2,1-d:1',2'-f][1,3]dioxepine

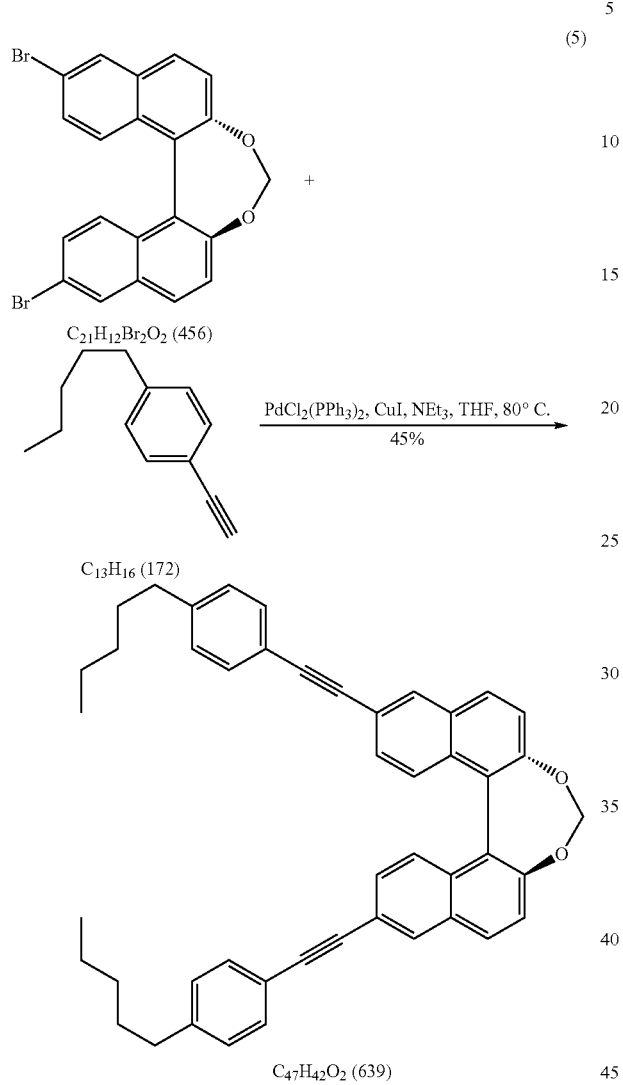

(S)-9,14-Dibromodinaphtho[2,1-d:1',2'-f][1,3]dioxepine (0.65 g, 1.43 mmol) is stirred under nitrogen in triethylamine (3 ml) and THF (5 ml). A catalytic amount of PdCl$_2$(PPh$_3$)$_2$ and CuI is added and the reaction stirred at 80° C. 1-ethynyl-4-pentyl benzene (0.52 g, 2.99 mmol) in THF (5 ml) is added very slowly over 3 hours and the reaction stirred for 72 hours with addition of extra 1-ethynyl-4-pentyl benzene (1.00 ml, 5.81 mmol) in THF, triethylamine, PdCl$_2$(PPh$_3$)$_2$ and CuI over this time. On completion the solution is diluted with DCM and poured onto water. Layers are separated and extracted with DCM (×2); organics are combined and washed with brine (×2) and dried over sodium sulphate. Excess solvents are removed in vacuo to yield a brown solid, which is purified using FlashMaster column chromatography (SiO$_2$, 20% DCM/petrol), which removed the brown colour. The product is further purified using FlashMaster column chromatography (C18 reverse phase, 100% acetonitrile, running up to 10% DCM/acetonitrile) to yield compound 15 as a white solid (0.41 g, 0.64 mmol, 45%).

M.p. 167° C. $^1$H NMR and $^{13}$C NMR give expected signals. HTP=57 (5% concentration in BLO87, give a right handed twist)

EXAMPLE 6

Compound (6) is prepared as described below.

(S)-10,15-bis((4-pentylphenyl)ethynyl)-4,5-dihydrodinaphtho[2,1-e:1',2'-g][1,4]dioxocine

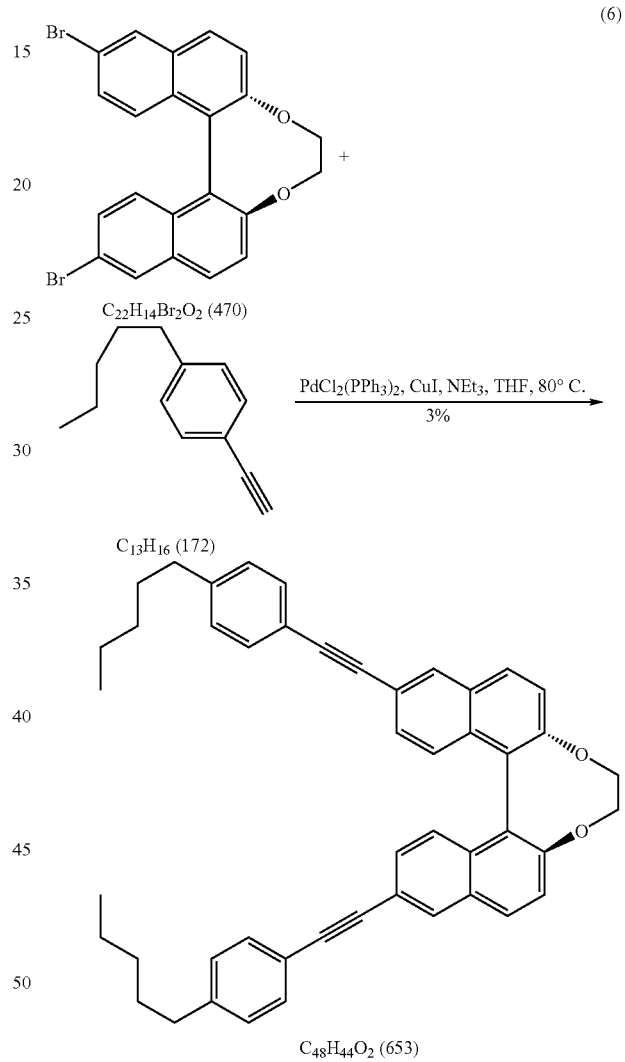

(S)-10,15-Dibromo-4,5-dihydrodinaphtho[2,1-e:1',2'-g][1,4]dioxocine (2.00 g, 4.25 mmol) is stirred under nitrogen in triethylamine (3 ml) and THF (5 ml). A catalytic amount of PdCl$_2$(PPh$_3$)$_2$ and CuI is added and the reaction stirred at 80° C. 1-ethynyl-4-pentyl benzene (1.47 g, 8.51 mmol) in THF (5 ml) is added very slowly over 3 hours and the reaction stirred for 72 hours with addition of extra 1-ethynyl-4-pentyl benzene (2×0.50 g, 5.81 mmol) in THF and triethylamine over this time. On completion the solution is diluted with DCM and poured onto water. Layers are separated and extracted with DCM (×2); organics are combined and washed with water (×2) and dried over sodium sulphate. Excess solvents are removed in vacuo to yield a brown solid, which is purified by using an SP Flash Purification System (SiO$_2$, 2% ethyl acetate/n-hexane, running up to 20% ethyl acetate/n-hexane), which removed the brown colour. The product is further purified using the same system (C18 reverse phase, 50% acetonitrile/water, running up to 100% acetonitrile) to yield an off-white solid (0.07 g, 0.1 mmol, 3%).

M.p. 161° C. $^1$H NMR and $^{13}$C NMR give expected signals. HTP=52 (5% concentration in BLO87, give a right handed twist)

EXAMPLE 7

Compound (7) is prepared as described below.

(S)-2,7-bis((4-pentylphenyl)ethynyl)-13,14-dihydro-12H-dinaphtho[2,1-f:1',2'-h][1,5]dioxonine

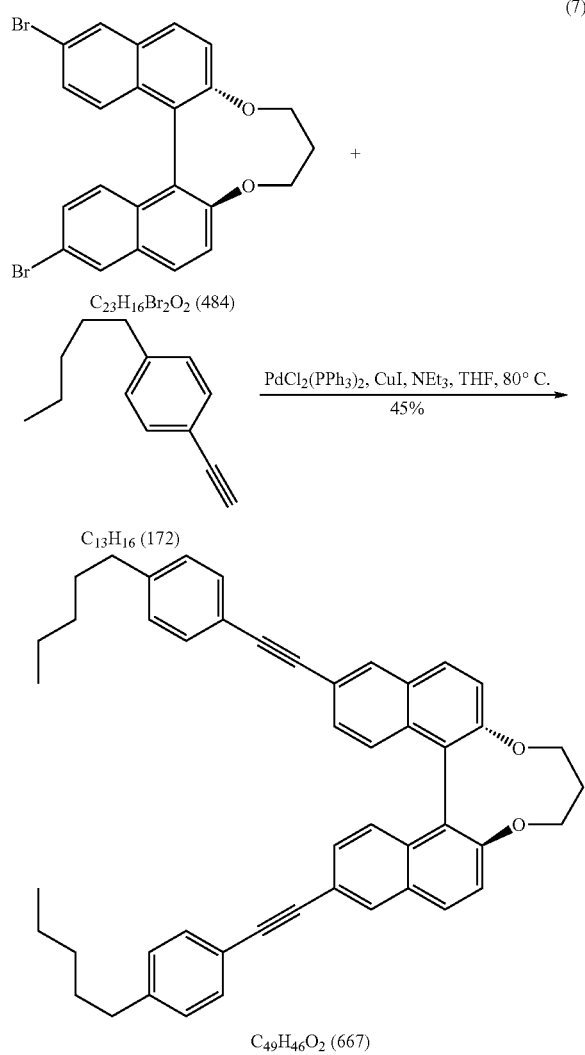

(S)-2,7-Dibromo-13,14-dihydro-12H-dinaphtho[2,1-f:1', 2'-h][1,5]dioxonine (1.00 g, 2.07 mmol) is stirred under nitrogen in triethylamine (3 ml) and THF (5 ml). A catalytic amount of PdCl$_2$(PPh$_3$)$_2$ and CuI is added and the reaction stirred at 80° C. 1-ethynyl-4-pentyl benzene (0.71 ml, 4.13 mmol) in THF (5 ml) is added very slowly over 3 hours and the reaction stirred for 20 hours. On completion the solution is diluted in DCM and poured onto water. Layers are separated and extracted with DCM (×2), organics are combined and washed with water (×2), dried over sodium sulphate and excess solvents removed in vacuo to yield a brown solid, which is purified by FlashMaster column chromatography (SiO$_2$, 10% DCM/petrol, running up to 40% DCM/petrol). The columned product shows an impurity at 12 minutes by HPLC and is further purified by preparative HPLC (100 ml/minute, 20% water in acetonitrile, running up to 100% acetonitrile after ten minutes) to yield compound 17 as a white solid (0.62 g, 0.93 mmol, 45%).

M.p. 47° C. $^1$H NMR and $^{13}$C NMR give expected signals. HTP=48 (5% concentration in BLO87, give a right handed twist)

EXAMPLE 8

Compound (8) is prepared as described below.

(S)-5,5'-(4,5-dihydrodinaphtho[2,1-e:1',2'-g][1,4]-dioxocine-10,15-diyl)dipent-4-yn-1-ol

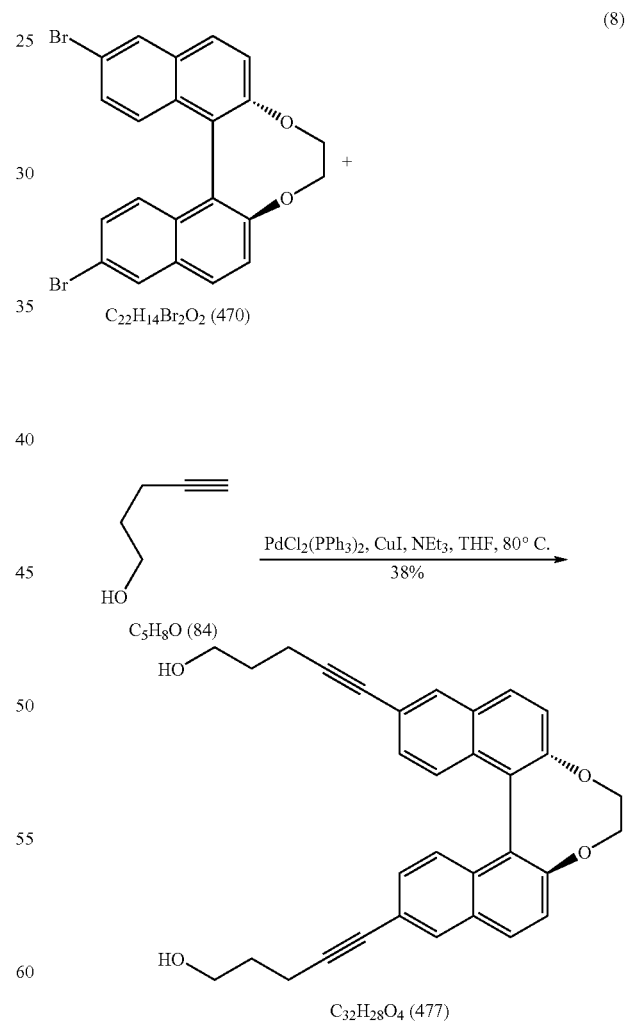

(S)-10,15-Dibromo-4,5-dihydrodinaphtho[2,1-e:1',2'-g][1,4]dioxocine (2.00 g, 4.25 mmol) is stirred under nitrogen in triethylamine (6 ml) and THF (10 ml). A catalytic amount of PdCl$_2$(PPh$_3$)$_2$ and CuI is added and the reaction stirred at 80° C. 4-Pentyn-1-ol (0.75 g, 8.93 mmol) in THF (10 ml) is added very slowly over 3 hours and the reaction stirred for 48 hours with addition of additional THF and triethylamine as the solvent evaporated and 4-Pentyn-1-ol (1.00 ml, 11.89 mmol), PdCl$_2$(PPh$_3$)$_2$ and CuI to ensure completion of reaction. Over time the solution darkens to a brown colour. On completion the solution is diluted in DCM and poured onto water. Layers are separated and extracted with DCM (×2), organics are combined and washed with brine (×2), dried over sodium sulphate and excess solvents removed in vacuo to yield a yellow/brown oil, which is purified by FlashMaster column chromatography (SiO$_2$, 100% DCM, running up to 60% DCM/ethyl acetate) to yield both the mono- and di-substituted products. The product is purified by FlashMaster column chromatography (SiO$_2$, 40% ethyl acetate in petrol, running up to 100% ethyl acetate before running through with propanol) to yield a cream oil (0.77 g, 1.62 mmol, 38%).

3-Chloro-propionic Acid 3-(4-chlorocarbonyl-phenoxy)-propyl Ester

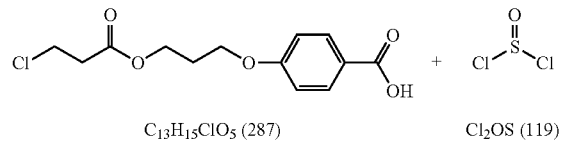

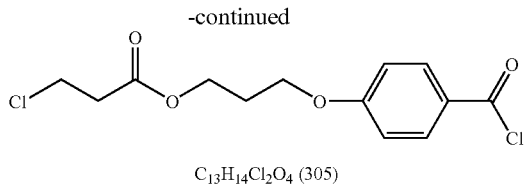

C$_{13}$H$_{14}$Cl$_2$O$_4$ (305)

HPBA-3-chloropropionate (5.00 g, 17.44 mmol) is dissolved in DCM (160 ml). NMP (0.5 ml, 5.04 mmol) is added and the materials are stirred under nitrogen until complete dissolution had occurred. Thionyl chloride (2.49 g, 20.93 mmol) is added and the reaction stirred under nitrogen overnight at 35° C. On completion the reaction turns clear yellow and excess solvents are removed in vacuo to yield a dark yellow oil (6.02 g, 19.73 mmol, 113% (contained NMP)).

$^1$H NMR and FT-IR give expected signals.

EXAMPLE 9

Compound (9) is prepared as described below.

(S)-6,6'-(4,5-dihydrodinaphtho[2,1-e:1',2'-g][1,4]dioxocine-10,15-diyl)bis(Pent-4-yne-5,1-diyl)bis(4-(3-(acryloyloxy)propoxy)benzoate)

(9)

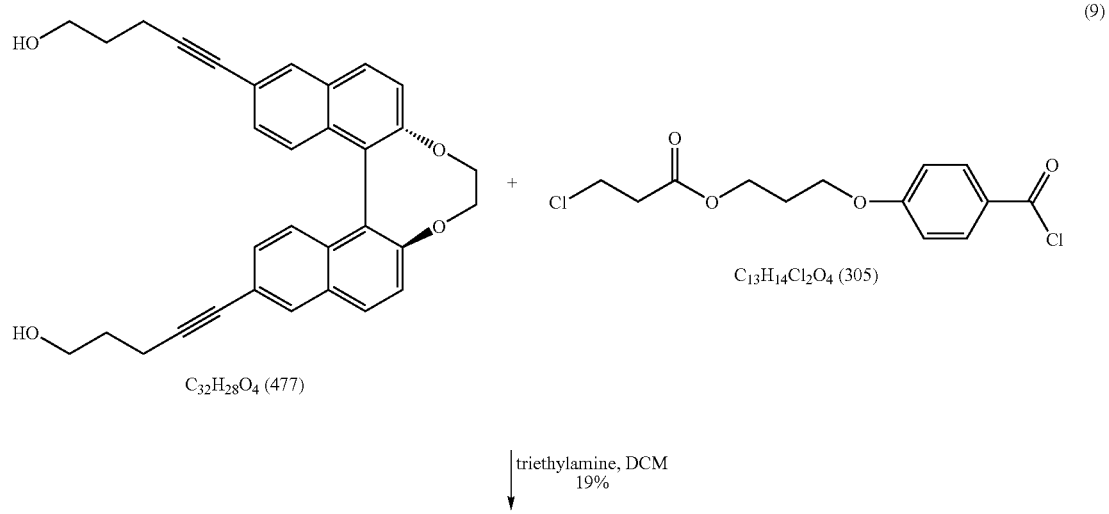

-continued

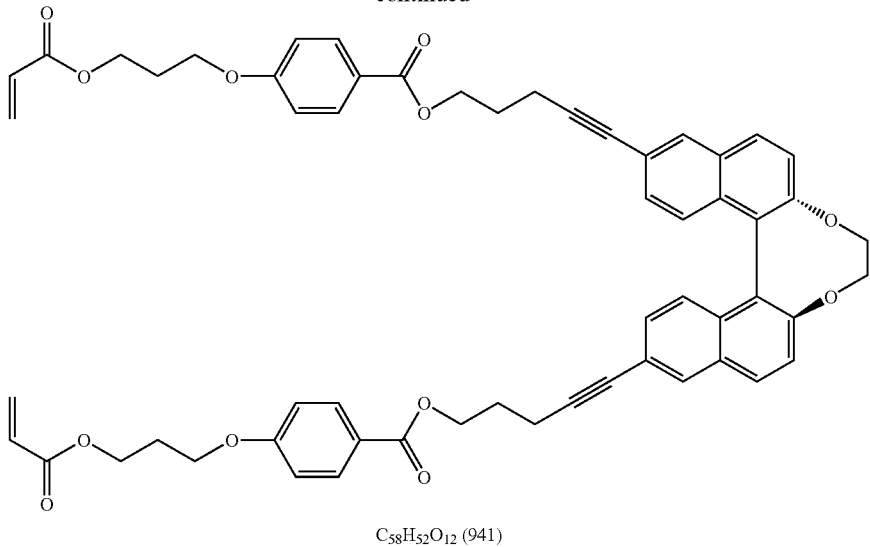

C₅₈H₅₂O₁₂ (941)

(S)-5,5'-(4,5-Dihydrodinaphtho[2,1-e:1',2'-g][1,4]dioxocine-10,15-diyl)dipent-4-yn-1-ol (0.77 g, 1.62 mmol) and 3-Chloro-propionic acid 3-(4-chlorocarbonyl-phenoxy)-propyl ester (1.18 g, 3.39 mmol (88% content)) are dissolved in DCM (60 ml) and stirred under nitrogen. Triethylamine (1.96 ml, 19.39 mmol) is added slowly with evolution of white HCl gas and the reaction heated to 35° C. and stirred for overnight. On completion the reaction mixture is cooled to r.t., diluted with DCM and poured onto water. Layers are separated and extracted with DCM (×2) before the organic phases are combined and washed with brine (×3) and dried over sodium sulphate. Excess solvents are removed in vacuo to yield the product as a brown oil (1.36 g), 28% pure by HPLC. The crude product is purified by FlashMaster column chromatography (SiO₂, 20% ethyl acetate/petrol), however; all materials come off together, but the brown colour is removed so the fractions are recombined. The product is purified again by preparative HPLC (80 ml/minute, 50% water in acetonitrile for five minutes, running up to 100% acetonitrile after fifteen minutes) to yield an off-white solid (0.29 g, 0.31 mmol, 19%).

M.p. 33° C. $^1$H NMR and $^{13}$C NMR give expected signals. HTP=15 (10% concentration in BLO87, give a right handed twist).

The invention claimed is:
1. A compound of formula I

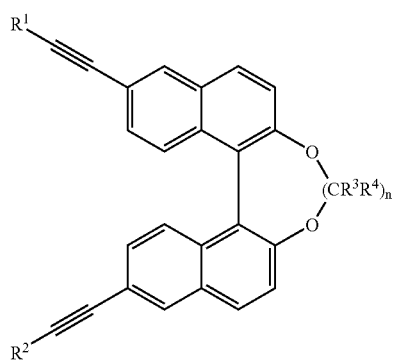

I wherein
$R^1$ and $R^2$ independently of each other denote H, F, Cl, Br, I, CN, NCS, SF₅, or straight-chain, branched or cyclic alkyl, aryl or heteroaryl having 1 to 30 C-atoms that is optionally mono- or polysubstituted by F, Cl, Br, I or CN, and in which one or more non-adjacent CH₂ groups are optionally replaced, in each case independently from one another, by —O—, —S—, —NH—, —NR⁰—, —SiR⁰R⁰⁰—, —CO—, —COO—, —OCO—, —OCO—O—, —S—CO—, —CO—S—, —CY¹=CY²— or —C≡C— in such a manner that O and/or S atoms are not linked directly to one another, or denote -(Z¹-A¹)$_m$-R⁵ or P-Sp-, $R^3$ and $R^4$ independently of each other have one of the meanings of $R^1$, $R^5$ is H, F, Cl, Br, I, CN, NCS, SF₅, or straight-chain or branched alkyl having 1 to 30 C-atoms that is optionally mono- or polysubstituted by F, Cl, Br, I or CN, and in which one or more non-adjacent CH₂ groups are optionally replaced, in each case independently from one another, by —O—, —S—, —NH—, —NR⁰—, —SiR⁰R⁰⁰—, —CO—, —COO—, —OCO—, —OCO—O—, —S—CO—, —CO—S—, —CY¹=CY²— or —C≡C— in such a manner that O and/or S atoms are not linked directly to one another, or denotes P-Sp-, P is a polymerizable group,
Sp is a spacer group or a single bond,
$A^1$ is in case of multiple occurrence independently of one another an aromatic or alicyclic group, which optionally contains one or more hetero atoms selected from N, O and S, and is optionally mono- or polysubstituted by $R^1$, $Z^1$ in case of multiple occurrence independently of one another denotes —O—, —S—, —CO—, —COO—, —OCO—, —S—CO—, —CO—S—, —O—COO—, —CO—NR⁰—, —NR⁰—CO—, —NR⁰—CO—NR⁰⁰, —NR⁰—CO—O—, —O—CO—NR⁰—, —OCH₂—, —CH₂O—, —SCH₂—, —CH₂S—, —CF₂O—, —OCF₂—, —CF₂S—, —SCF₂—, —CH₂CH₂—, —(CH₂)₄—, —CF₂CH₂—, —CH₂CF₂—, —CF₂CF₂—, —CH=N—, —N=CH—, —N=N—, —CH=CR⁰—, —CY¹=CY²—, —C≡C—, —CH=CH—COO—, —OCO—CH=CH— or a single bond, R⁰ and R⁰⁰ independently of each other denote H or alkyl with 1 to 12 C-atoms, Y¹ and Y² independently of each other denote H, F, Cl or CN, m is 0, 1, 2, 3 or 4, n is an integer from 2 to 5, with the proviso that, if n is 3 and all R³ and R⁴ are H, then R¹ and R² are not 4-cyanophenyl.

2. A compound according to claim 1, comprising at least one group R¹, R² or R⁵ that is P-Sp.

3. A compound according to claim 1, wherein n is 2, 3, 4 or 5 and R³ and R⁴ are alkyl or alkoxy with 1 to 12 C atoms, or one or more groups CR³R⁴ denote CH-(Z¹-A¹)$_m$-R⁵.

4. A compound according to claim 1, wherein -(Z¹-A¹)$_m$- is independently

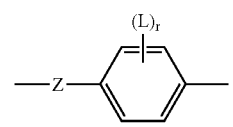
IIa

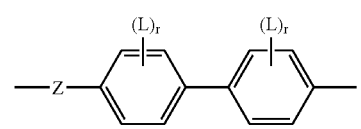
IIb

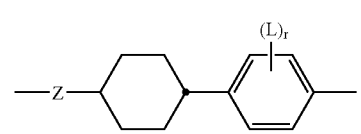
IIc

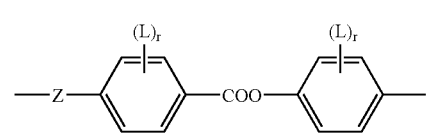
IId

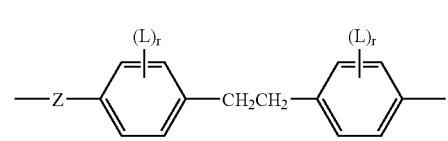
IIe

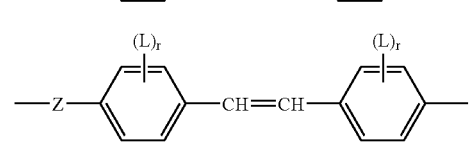
IIf

IIg

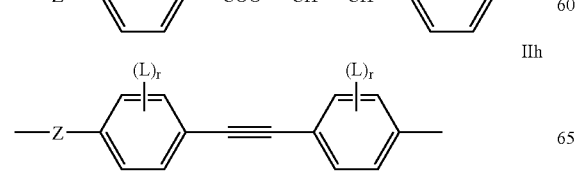
IIh

-continued

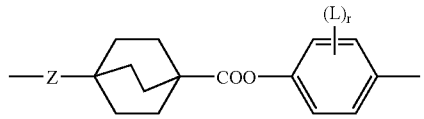
IIi

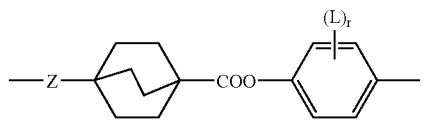
IIk or a mirror image thereof, wherein r is 0, 1, 2, 3 or 4, and L is independently H, F, Cl, Br, I, CN, NCS, SF₅, or straight-chain, branched or cyclic alkyl, aryl or heteroaryl having 1 to 30 C-atoms that is optionally mono- or polysubstituted by F, Cl, Br, I or CN, and in which one or more non-adjacent CH₂ groups are optionally replaced, in each case independently from one another, by —O—, —S—, —NH—, —NR⁰—, —SiR⁰R⁰⁰—, —CO—, —COO—, —OCO—, —OCO—O—, —S—CO—, —CO—S—, —CY¹=CY²— or —C≡C— in such a manner that O and/or S atoms are not linked directly to one another, or denote -(Z¹-A¹)$_m$-R⁵ or P-Sp-.

5. A compound according to claim 1, of the formulae

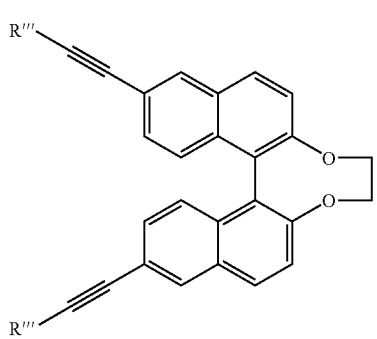
Ia

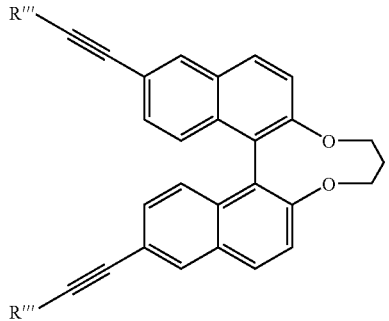
Ib

-continued
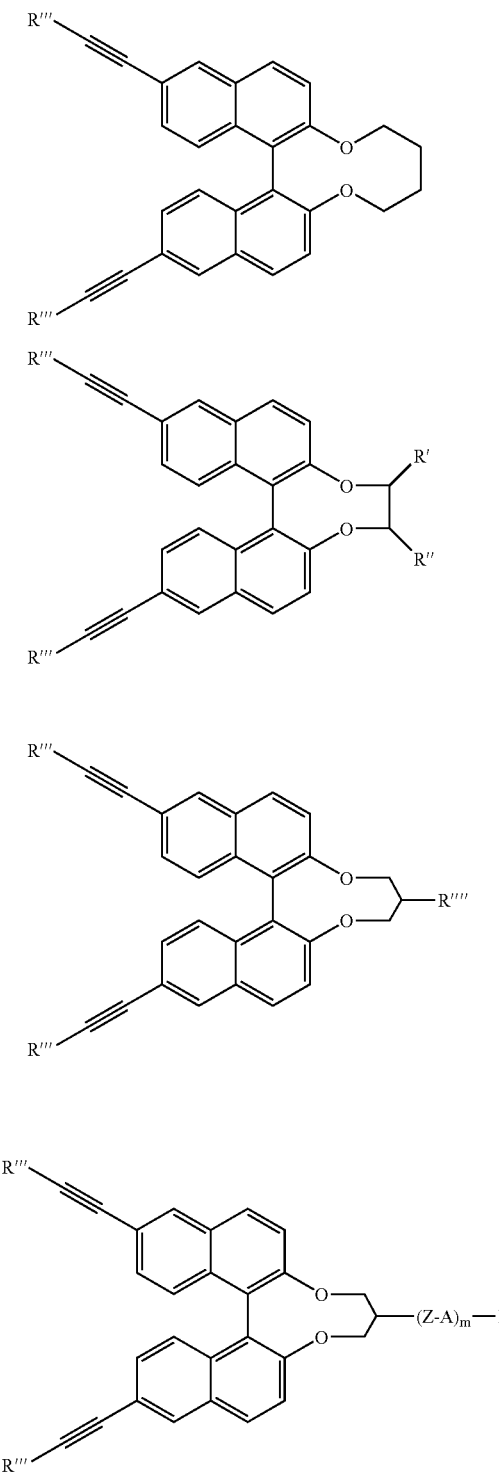
wherein
R' and R" have one of the meanings of $R^1$,
R''' is P-Sp- or has one of the meanings of $R^1$,
R'''' is P-Sp- or has one of the meanings of $R^1$,
Z has one of the meanings of $Z^1$, and
A has one of the meanings of $A^1$.
6. A compound according to claim 1, of the formulae
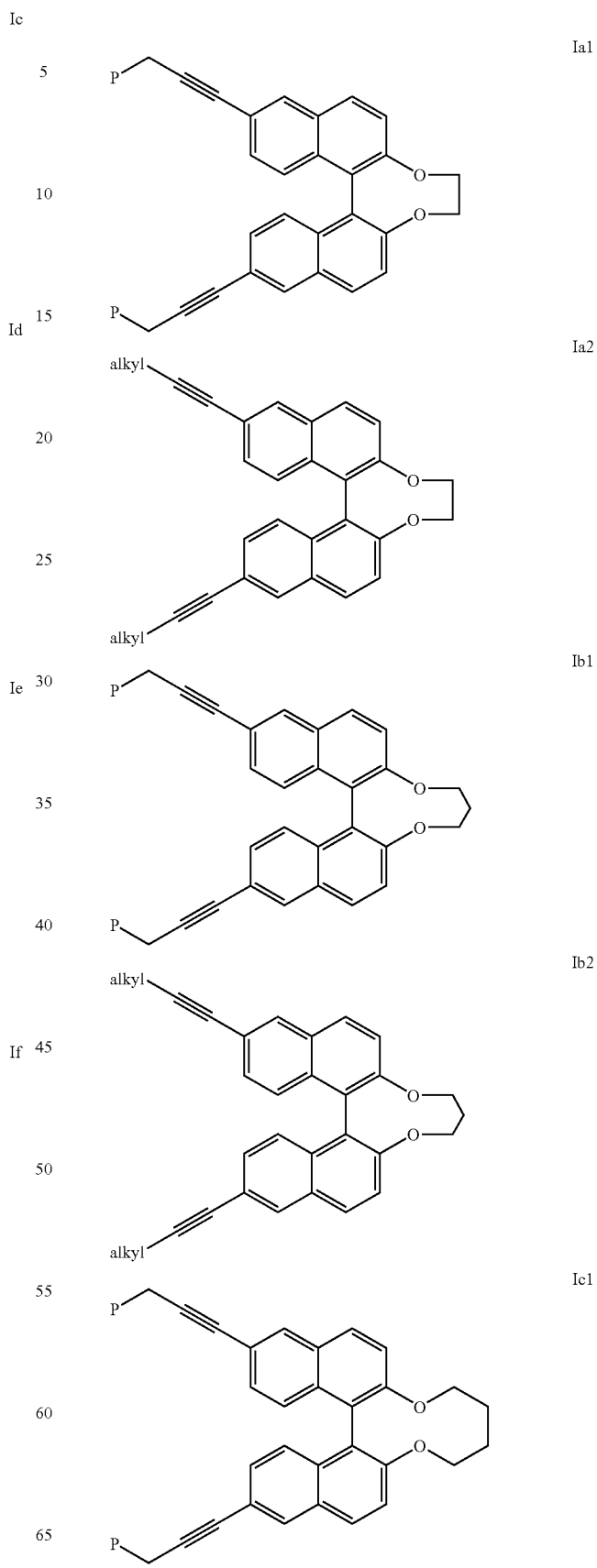

-continued
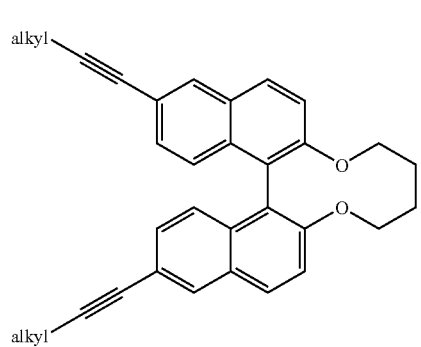
Ic2
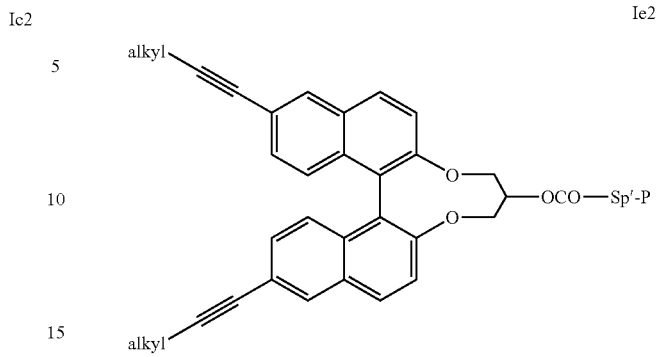
Ie2
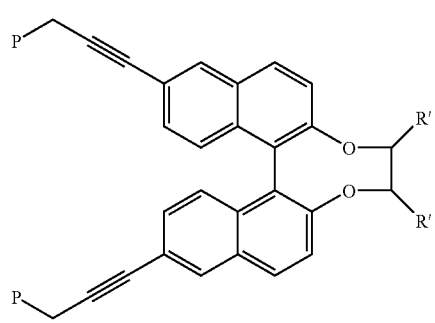
Id1
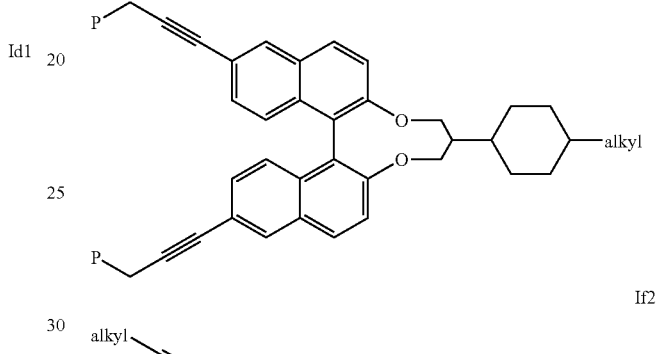
If1
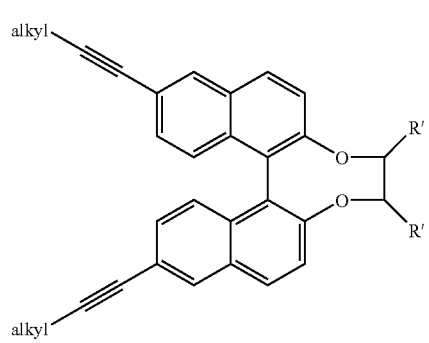
Id2
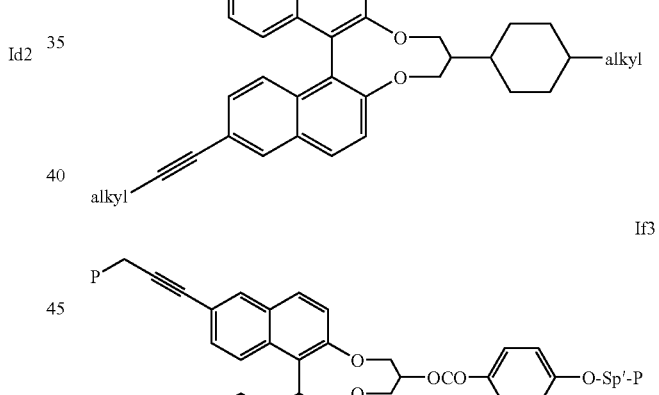
If2
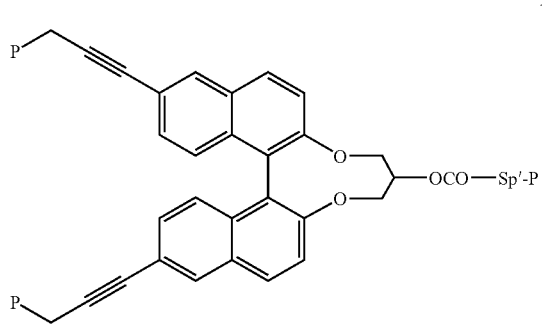
Ie1
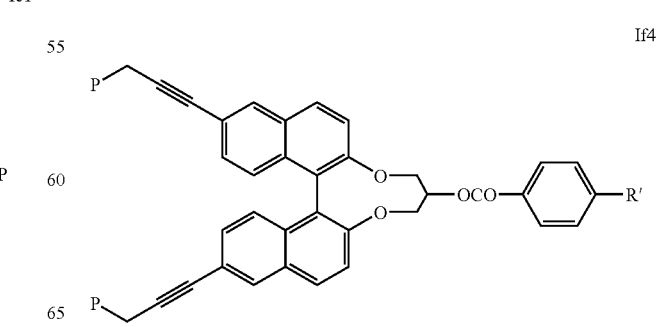
If3
or
If4 wherein R' is H, F, Cl, Br, I, CN, NCS, SF$_5$, or straight-chain, branched or cyclic alkyl, aryl or heteroaryl having 1 to 30 C-atoms that is optionally mono- or polysubstituted by F, Cl, Br, I or CN, and in which one or more non-adjacent CH$_2$ groups are optionally replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —CY$^1$=CY$^2$— or —C≡C— in such a manner that O and/or S atoms are not linked directly to one another, or denote -(Z$^1$-A$^1$)$_m$-R$^5$ or P-Sp-.

Sp' is alkylene with 1 to 20 C atoms, which is optionally mono- or polysubstituted by F, Cl, Br, I or CN, and wherein one or more non-adjacent CH$_2$ groups are optionally replaced, in each case independently from one another, by —O—, —S—, —NH—, —NR$^0$—, —SiR$^0$R$^{00}$—, —CO—, —COO—, —OCO—, —OCO—O—, —S—CO—, —CO—S—, —NR$^0$—CO—O—, —O—CO—NR$^0$—, —NR$^0$—CO—NR$^0$—, —CH=CH— or —C≡C— in such a manner that O and/or S atoms are not linked directly to one another, and alkyl is n-alkyl with 1 to 12 C atoms.

7. A liquid crystal mixture, comprising two liquid crystalline compounds wherein at least one compound is at least one compound according to claim 1.

8. A polymer or anisotropic polymer film obtained by polymerizing a compound or a mixture of compounds according to claim 1 in liquid crystal phase and/or in an oriented state.

9. Electrooptical displays, LCDs, optical films, polarizers, compensators, beam splitters, reflective films, alignment layers, color filters, holographic elements, hot stamping foils, colored images, decorative or security markings, LC pigments, adhesives, cosmetics, diagnostics, nonlinear optics, optical information storage, electronic devices, organic semiconductors, field effect transistors (FET), components of integrated circuitry (IC), thin film transistors (TFT), Radio Frequency Identification (RFID) tags, organic light emitting diodes (OLED), electroluminescent displays, lighting devices, photovoltaic devices, sensor devices, electrode materials, photoconductors, electrophotographic recording, lasing materials or devices, or chiral dopants comprising at least one compound according to claim 1.

10. A liquid crystal display, color filter, polarizer, retardation film, alignment layer, authentification, verification or security marking, colored image, object or document of value comprising a compound, mixture, polymer or polymer film according to claim 1.

11. A method of preparing a compound according to claim 1, comprising
   a) reacting binaphthol with bromine,
   b) reacting an intermediate 6,6'-dibromo-[1,1']binaphthalenyl-2,2'-diol with an alkyl ditosylate and potassium carbonate,
   c) reacting an resulting ring closed intermediate with an acetylene compound in the presence of a base, and a catalytic amount of a copper salt and a palladium catalyst to form desired product.

12. A liquid crystal mixture, comprising two liquid crystalline compounds wherein at least one compound is at least one compound according to claim 5.

13. A polymer or anisotropic polymer film obtained by polymerizing a compound or a mixture of compounds according to claim 5 in liquid crystal phase and/or in an oriented state.

14. Electrooptical displays, LCDs, optical films, polarizers, compensators, beam splitters, reflective films, alignment layers, colour filters, holographic elements, hot stamping foils, coloured images, decorative or security markings, LC pigments, adhesives, cosmetics, diagnostics, nonlinear optics, optical information storage, electronic devices, organic semiconductors, field effect transistors (FET), components of integrated circuitry (IC), thin film transistors (TFT), Radio Frequency Identification (RFID) tags, organic light emitting diodes (OLED), electroluminescent displays, lighting devices, photovoltaic devices, sensor devices, electrode materials, photoconductors, electrophotographic recording, lasing materials or devices, or chiral dopants comprising at least one compound according to claim 5.

15. A liquid crystal display, color filter, polarizer, retardation film, alignment layer, authentification, verification or security marking, colored image, object or document of value comprising a compound, mixture, polymer or polymer film according to claim 5.

16. A liquid crystal mixture, comprising two liquid crystalline compounds wherein at least one compound is at least one compound according to claim 4.

17. A polymer or anisotropic polymer film obtained by polymerizing a compound or a mixture of compounds according to claim 4 in liquid crystal phase and/or in an oriented state.

18. Electrooptical displays, LCDs, optical films, polarizers, compensators, beam splitters, reflective films, alignment layers, colour filters, holographic elements, hot stamping foils, coloured images, decorative or security markings, LC pigments, adhesives, cosmetics, diagnostics, nonlinear optics, optical information storage, electronic devices, organic semiconductors, field effect transistors (FET), components of integrated circuitry (IC), thin film transistors (TFT), Radio Frequency Identification (RFID) tags, organic light emitting diodes (OLED), electroluminescent displays, lighting devices, photovoltaic devices, sensor devices, electrode materials, photoconductors, electrophotographic recording, lasing materials or devices, or chiral dopants comprising at least one compound according to claim 4.

19. A liquid crystal display, color filter, polarizer, retardation film, alignment layer, authentification, verification or security marking, colored image, object or document of value comprising a compound, mixture, polymer or polymer film according to claim 4.

* * * * *